Figure 1:
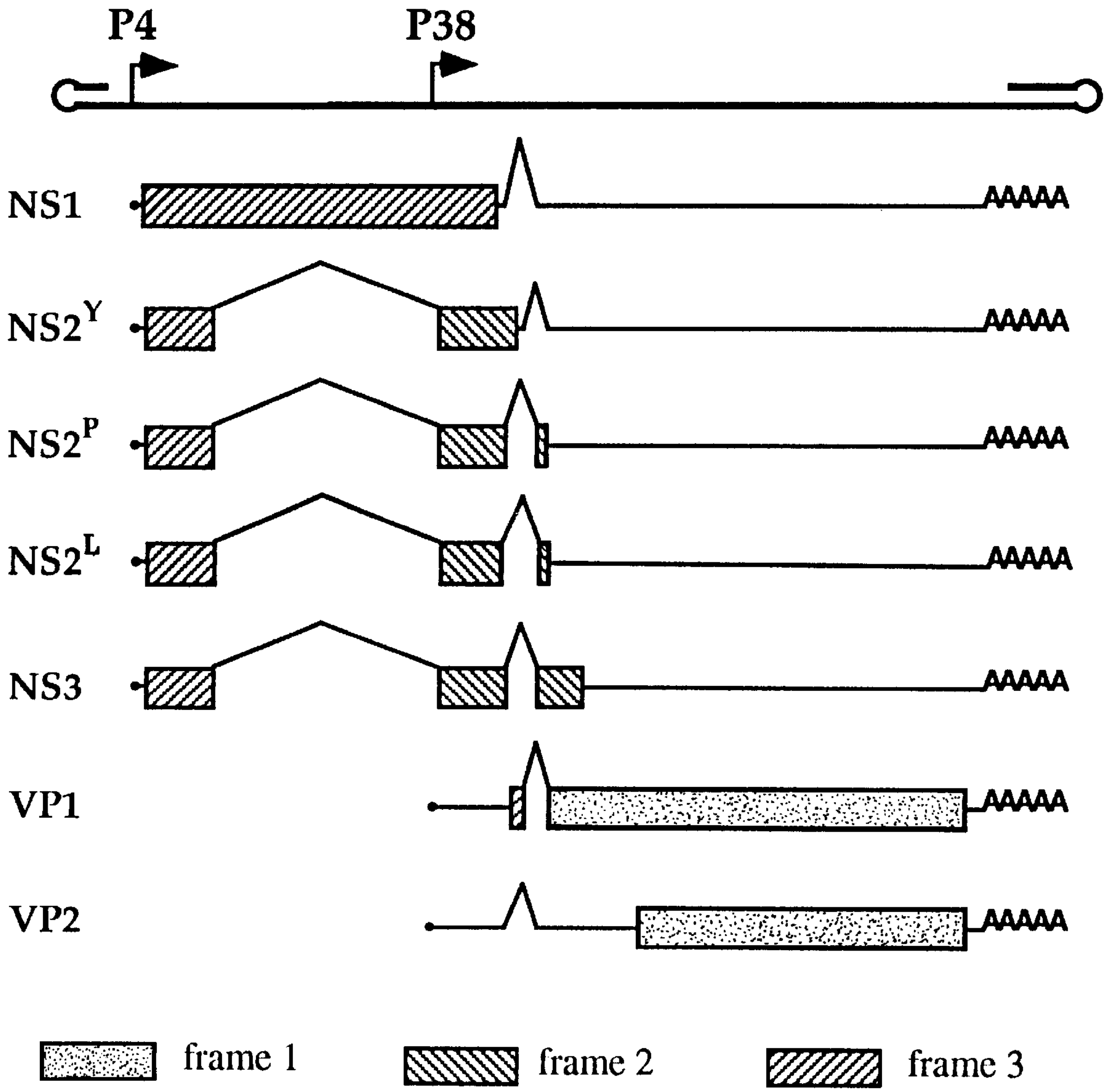

US005853716A

United States Patent [19]
Tattersall et al.

[11] Patent Number: 5,853,716
[45] Date of Patent: Dec. 29, 1998

[54] GENETICALLY ENGINEERED CHIMERIC VIRUSES FOR THE TREATMENT OF DISEASES ASSOCIATED WITH VIRAL TRANSACTIVATORS

[75] Inventors: Peter J. Tattersall; Susan F. Cotmore, both of Guilford, Conn.

[73] Assignee: Yale University, New Haven, Conn.

[21] Appl. No.: 690,174

[22] Filed: Jul. 25, 1996

Related U.S. Application Data

[60] Provisional application No. 60/001,611 Jul. 28, 1995.

[51] Int. Cl.$^6$ .................... A01N 63/00

[52] U.S. Cl. .................... 424/93.2; 424/93.6; 435/357; 435/372.3; 536/24.1

[58] Field of Search .................... 536/23.1, 23.4, 536/23.5, 23.52, 24.1, 24.5; 424/93.2, 93.6; 435/357, 372.3

[56] References Cited

U.S. PATENT DOCUMENTS

| | | | |
|---|---|---|---|
| 5,302,517 | 4/1994 | Rhode, III | 435/69.1 |
| 5,306,631 | 4/1994 | Harrison et al. | 435/172.3 |
| 5,474,935 | 12/1995 | Chatterjee et al. | 435/320.1 |
| 5,585,254 | 12/1996 | Maxwell et al. | 435/172.3 |

FOREIGN PATENT DOCUMENTS

| | | |
|---|---|---|
| WO 90/05538 | 5/1990 | WIPO . |
| WO 90/11359 | 10/1990 | WIPO . |
| WO 94/13823 | 6/1994 | WIPO . |

OTHER PUBLICATIONS

Cotmore and Tattersall, 1994, “An Asymmetric Nucleotide in the Parvoviral 3’ Hairpin Directs Segregation of a Single Active Origin of DNA Replication”, EMBO J. 13:4145–4152.

Koering et al., 1994, “Induced Expression of the Conditionally Cytotoxic Herpes Simplex Virus *thymidine kinases* Gene by Means of a Parvoviral Regulatory Circuit”, Hum. Gene Ther. 5:457–463.

Lee et al., 1994, “Inhibition of Human Immunodeficiency Virus Type 1 in Human T Cells by a Potent Rev Response Element Decoy Consisting of the 13–Nucleotide Minimal Rev–Binding Domain”, J. Virol. 68:8254–8264.

Mousset et al., 1994, “The Cytotoxicity of the Autonomous Parvovirus Minute Virus of Mice Nonstructural Proteins in FR3T3 Rat Cells Depends on Oncogene Expression”, J. Virol. 68:6446–6453.

Agbandje et al., 1993, “Structure Determination of Feline Panleukopenia Virus Empty Particles”, Proteins: Structure, Function and Genetics 16:155–171.

Bahner et al., 1993, “Comparison of *Trans*–Dominant Inhibitory Mutant Human Immunodeficiency Virus Type 1 Genes Expressed by Retroviral Vectors in Human T Lymphocytes”, J. Virol. 67:3199–3207.

Buonocore and Rose, 1993, “Blockade of Human Immunodeficiency Virus Type 1 Production in $CD4^+$ T Cells by an Intracellular CD4 Expressed Under Control of the Viral Long Terminal Repeat”, Proc. Natl. Acad. Sci. USA 90:2695–2699.

Cotmore et al., 1993, “Asymmetric Resolution of a parvovirus Palindrome in Vitro”, J. Virol. 67:1579–1589.

Dear et al., 1993, “The HOX11 Gene Encodes a DNA–Binding Nuclear Transcription Factor Belonging to a Distinct Family of Homeobox Genes”, Proc. Natl. Acad. Sci. USA 90:4431–4435.

Diffoot et al., 1993, “The Complete Nucleotide Sequence of Parvovirus LuIII and Localization of a Unique Sequence Possibly Responsible for Its Encapsidation Pattern”, Virology 192:339–345.

Liem et al., 1993, “The Development and Testing of Retroviral Vectors Expressing *trans*–Dominant Mutants of HIV–1 Proteins to Confer Anti–HIV–1 Resistance”, Hum. Gene Ther. 4:625–634.

Sakai et al., 1993, “Compatibility of Tat and Rev Transactivators in the Primate Lentiviruses”, Arch. Virol. 129:1–10.

Sarver and Rossi, 1993, “Gene Therapy: A Bold Direction for HIV–1 Treatment”, AIDS Res. Hum. Retroviruses 9:483–487.

Sheldon et al., 1993, “Characterization of the Inducer of Short Transcripts, A Human Immunodeficiency Virus Type 1 Transcriptional Element That Activates the Synthesis of Short RNAs”, Mol. Cell Biol. 13:1251–1263.

Wu and Rossmann, 1993, “The Canine Parvovirus Empty Capsid Structure”, J. Mol. Biol. 233:321–244.

Yoshida, 1993, “HTLV–1 Tax: Regulation of Gene Expression and Disease”, Trends Microbiol. 1:131–135.

Zenzie–Gregory et al., 1993, “HIV–1 Core Promoter Lacks a Simple Initiator Element but Contains a Bipartite Activator at the Transcription Start Site”, J. Biol. Chem. 268:15823–15832.

Berkhhout and Jeang, 1992, “Functional Roles for the TATA Promoter and Enhancers in Basal and Tat–Induced Expression of the Human Immunodeficiency Virus Type 1 Long Terminal Repeat”, J. Virol. 66:139–149.

Bevec et al., 1992, “Inhibition of Human Immunodeficiency Virus Type 1 Replication in Human T Cells by Retroviral––Mediated Gene Transfer of a Dominant–Negative Rev Trans–Activator”, Proc. Natl. Acad. Sci. USA 89:9870–9874.

(List continued on next page.)

*Primary Examiner*—James Ketter
*Assistant Examiner*—Irem Yucel
*Attorney, Agent, or Firm*—Pennie & Edmonds LLP

[57] ABSTRACT

The present invention relates to chimeric viruses, the replication of which is regulated by a transactivation signal produced by diseased host cells. The chimeric viruses of the invention can infect both normal and diseased host cells. However, the chimeric virus replicates efficiently in and kills diseased host cells that produce the transactivation signal. The use of such chimeric viruses to treat infectious diseases and cancers are described. A particularly useful embodiment involves the modification of a murine parvovirus that infects human T cells to generate a chimeric parvovirus that is cytocidal to human T cells that express HIV-tat. The chimeric parvovirus can be used to treat HIV-infection.

12 Claims, 12 Drawing Sheets

OTHER PUBLICATIONS

Buchschacher Jr. and Panganiban, 1992, "Human Immunodeficiency Virus Vectors for Inducible Expression of Foreign Genes", J. Virol. 66:2731–2739.

Chatterjee et al., 1992, "Dual–Target Inhibition of HIV–1 in Vitro by Means of an Adeno–Associated Virus Antisense Vector", Science 258:1485–1488.

Cotmore et al., 1992, "In vitro Excision and Replication of 5' Telomeres of Minute Virus of Mice DNA from Cloned Palindromic Concatemer Junctions", Virology 190:365–377.

Cullen and Garrett, 1992, "A comparison of Regulatory Features in Primitive Lentiviruses", AIDS Res. Hum. Retroviruses 8:387–393.

Kretzner et al., 1992, "Myc and Max Proteins Possess Distinct Transcriptional Activites", Nature 359:426–429.

Malim et al:, 1992, "Stable Expression of Transdominant Rev Protein in Human T Cells Inhibits Human Immunodeficiency Virus Replication", J. Exp. Med. 176:1197–1201.

Ojwang et al., 1992, "Inhibition of Human Immunodeficiency Virus Type 1 Expression by a Hairpin Ribozyme", Proc. Natl. Acad. Sci. USA 89:10802–10806.

Olsen et al., 1992, "Contribution of the TATA Motif to Tat–Mediated Transcriptional Activation of Human Immunodeficiency Virus Gene Expression", J. Virol. 66:5594–5597.

Prendergast and Ziff, 1992, "A New Bind for Myc", Trends in Genetics 8:91–96.

Russell et al., 1992, "Transformation–Dependent Expression of Interleukin Genes Delivered by a Recombinant Parvovirus", J. Virol. 66:2821–2828.

Sczakiel et al., 1992, "Tat–and Rev–Directed Antisense RNA Expression Inhibits and Abolishes Replication of Human Immunodeficiency Virus Type 1: A Temporal Analysis", J. Virol. 66:5576–5581.

Pitluk and Ward, 1991, "Unusual Sp 1–GC Box Interaction in a Parvovirus Promoter", J. Virol. 65:6661–6670.

Rittner and Sczakiel, 1991, "Identification and Analysis of Antisense RNA Target Regions of the Human Immunodeficiency Virus Type 1", Nucleic Acids Res. 19:1421–1426.

Rommelaere et al., 1991, "Antineoplastic Activity of Parvoviruses", J. Virol. Meth. 333:233–251.

Tsao et al., 1991, "The Three–Dimensional Structure of Canine Parvovirus and Its Functional Implications", Science 251:1456–1464.

Buonocore and Rose, 1990, "Prevention of HIV–1 Glycoprotein Transport by Soluble CD4 Retained in the Endoplasmic Reticulum", Nature 345:625–628.

Rommelaere et al., 1990, "Oncosuppression by Parvoviruses", Handbook of Parvoviruses pp. 41–58.

Doerig et al., 1988, "Minute Virus of Mice Non–Structural Protein NS–1 is Necessary and Sufficient for *Trans*–Activation of the Viral p39 Promoter", J. Gen Virol. 69:2563–2573.

Maio and Brown, 1988, "Regulation of Expression Driven by Human Immunodeficiency Virus Type 1 and Human T–Cell Leukemia Virus Type 1 Long Terminal Repeats in Pluripotential Human Embryonic Cells", J. Virol. *62*:1398–1407.

Spandau and Lee, 1988, "*trans*–Activation of Viral Enhancers by the Hepatitis B Virus X Protein", J. Virol. 62:427–434.

Zahm et al., 1988, "The HBV X–ORF Encodes a Transactivator: A Potential Factor in Viral Hepatocarcinogenesis", Oncogene 3:169–177.

Cotmore and Tattersall, 1987, "The Autonomously Replicating Parvoviruses of Vertebrates", Adv. Virus Res. 33:91–174.

Cullen, 1986, "*Trans*–Activation of Human Immunodeficiency Virus Occurs via a Bimodal Mechanism", Cell 46:973–982.

Ben–Asher and Aloni, 1984, "Transcription of Minute Virus of Mice, and Autonomous Parvovirus, May Be Regulated by Attenuation", J. Virol. 52:266–276.

Tattersall and Bratton, 1983, "Reciprocal Productive and Restrictive Virus–Cell Interactions of Immunosuppressive and Prototype Strains of Minute Virus of Mice", J. Virol. *46*:944–955.

Roizman et al., 1981, "Herpesviridae. Definition, Provisional Nomenclature and Taxonomy", Intervirology 16:201–217.

Tattersall and Shatkin, 1977, "Sequence Homology Between the Structural Polypeptides of Minute Virus of Mice", J. Mol. Biol. 111:375–394.

Tattersall et al., 1976, "Three Structural Polypeptides Coded for by Minute Virus of Mice, a Parvovirus", J. Virol. 20:273–289.

Toolan, 1966, "Susceptibility of the Rhesus Monkey (*Macaca mulatta*) to H–1 Virus", Nature 209:833–834.

Toolan et al., 1966, "H–1 Virus Viremia in the Human", Proc. Soc. Expt'l. Biol. Med. 119:711–715.

Monif et al., 1965, "The H–1 and the RV Viruses and Pregnancy: Serological Study of Certain Groups of Pregnant Women", J. Pediat. 67:253–256.

Su, Y, et al., 1995, J. Virology, vol. 69, No. 1, pp. 110–121.

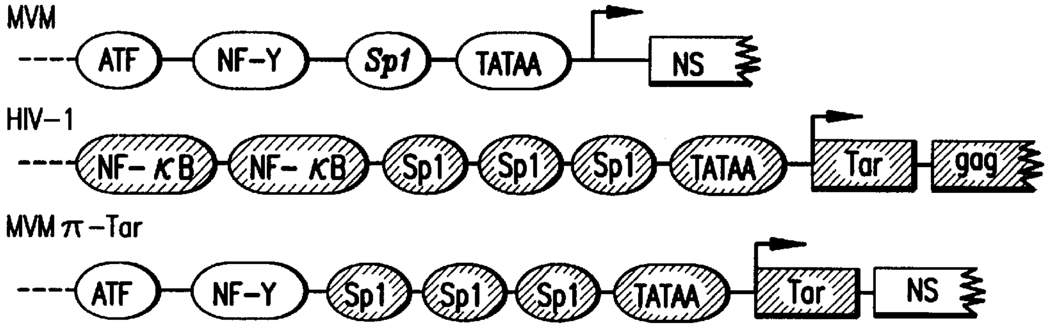

FIG.2A

PmeI

MVM 101 GTCAGTTCTA AAAATGATAA GCGGTTCAGG GAGTTTAAAC CAAGGCGCGA

MVM 151 AAAGGAAGTG GGCGTGGTTT AAAGTATATA AGCAACTACT GAAGTCAGTT

+1

MVM 201 ACTTATCTTT TCTTTCATTC TGTGAGTCGA GACGCACAGA AAGAGAGTAA

MVM 251 CCAACTAACC ATGGCTGGAA ATGCTTACTC TGATGAAGTT TTGGGAGCAA

FIG.2B

HIV -120 ATCGAGCTTG CTACAAGGGA CTTTCCGCTG GGGACTTTCC AGGGAGCGTG

HIV -70 GCCTGGGCGG GACTGGGGAG TGGCGAGCCC TCAGATGCTG CATATAAGCA

+1

HIV -20 GCTGCTTTTT GCCTGTACTG GGTCTCTCTG GTTAGACCAG ATCTGAGCCT

HIV 31 GGGAGCTCTC TGGCTAACTA GAGAACCCAC TGCTTAAGCC TCAATAAAGC

HIV 81 TTGCCTTGAG TGCTTC

FIG.2C

PmeI

MVM 101 GTCAGTTCTA AAAATGATAA GCGGTTCAGG GAGTTTAAAC GGGAGCGTG

HIV -70 GCCTGGGCGG GACTGGGGAG TGGCGAGCCC TCAGATGCTG CATATAAGCA

+1

HIV -20 GCTGCTTTTT GCCTGTACTG GGTCTCTCTG GTTAGACCAG ATCTGAGCCT

KpnI

HIV 31 GGGAGCTCTC TGGCTAACTA GAGAACCCAG AGgGTAcCCA ACTAACCATG

MVM 264 GCTGGAAATG CTTACTCTGA TGAAGTTTTG GGAGCAA

FIG.2D

MVM recombinants ▣ indicates the position of the 65bp repeat sequences.

324K B6-13S + pHIV*LacZ*

324K Tat-A3 + pHIV*LacZ*

GENETICALLY ENGINEERED CHIMERIC VIRUSES FOR THE TREATMENT OF DISEASES ASSOCIATED WITH VIRAL TRANSACTIVATORS

This application claims benefit of Provisional Application Ser. No. 60/001,611, filed Jul. 28, 1995.

TABKE OF CONTENTS

1. INTRODUCTION
2. BACKGROUND OF THE INVENTION
2.1. GENE THERAPY
2.2. THE HUMAN IMMUNODEFICIENCY VIRUS
2.3. HIV TREATMENT
2.4. PARVOVIRUS
3. SUMMARY OF THE INVENTION
4. BRIEF DESCRIPTION OF THE DRAWINGS
5. DETAILED DESCRIPTION OF THE INVENTION
5.1. ENGINEERING THE CHIMERIC VIRUS
5.1.1. CONSTRUCTION OF CYTOCIDAL CHIMERIC VIRUSES
5.1.2. CONSTRUCTION OF CYTOCIDAL-ANTAGONIST CHIMERIC VIRUSES
5.1.3. CONSTRUCTION OF NON-CYTOCIDAL-ANTAGONIST CHIMERIC VIRUSES
5.2. PRODUCTION OF RECOMBINANT VIRUS STOCKS
5.3. IN VITRO TESTING OF CHIMERIC VIRUSES
5.3.1. SCREENING RECOMBINANT VIRAL REPLICATION AND CYTOTOXICITY IN A PANEL OF DIVERSE CELL TYPES
5.3.2. TESTING OF RECOMBINANT CHIMERIC VIRUSES IN ANIMAL MODELS
5.4. USES OF CHIMERIC VIRUSES
6. EXAMPLE: CONSTRUCTION OF TAT-DEPENDENT, HUMAN LYMPHOTROPIC PARVOVIRUSES
6.1. MATERIALS AND METHODS
6.1.1. CELL LINES AND PRIMARY CULTURES
6.1.2. CHIMERIC VIRAL CONSTRUCTS
6.1.3. SOUTHERN BLOT ANALYSIS
6.1.4. WESTERN BLOT ANALYSIS
6.1.5. CYTOTOXICITY ASSAY
6.2. RESULTS
6.2.1. CONSTRUCTION OF RECOMBINANT VECTORS COMPOSED OF PARVOVIRAL AND HIV REGULATORY REGIONS
6.2.2. CONSTRUCTION OF TAT PRODUCER CELL LINES
6.2.3. EXPRESSION OF CHIMERIC VIRUSES IN PRODUCER CELL LINES
6.2.4. REPLICATION AND CYTOTOXIC EFFECTS OF CHIMERIC VIRUSES IN HUMAN LYMPHOCYTES
7. EXAMPLE: ISOLATION OF TARGET CELLS FROM WHOLE BLOOD AND INFECTION WITH CHIMERIC VIRUS
7.1. MATERIALS AND METHODS

1. INTRODUCTION

The present invention relates to chimeric viruses, the replication of which is regulated by a transactivation signal produced by diseased host cells. The chimeric viruses of the invention can infect both normal and diseased host cells.

However, the chimeric virus replicates efficiently in and selectively kills diseased host cells that produce the transactivation signal. The use of such chimeric viruses to treat infectious diseases and cancers are described. A particularly useful embodiment involves the modification of a murine parvovirus that infects human T cells to generate a chimeric parvovirus that is cytocidal to human T cells that express HIV-tat. The chimeric parvovirus can be used to treat HIV-infection.

2. BACKGROUND OF THE INVENTION

2.1. GENE THERAPY

Recent progress has been made in the field of gene therapy and the utilization of viral vectors as vehicles to introduce gene products into host cells. In the treatment of viral infections, a number of groups have manipulated viral vectors to introduce toxic gene products into cells. Replication defective vectors have been designed to introduce cell growth inhibitory genes into host cells (WO 90/12087, Oct. 18, 1980). One strategy attempted by several groups involves the use of the herpes simplex virus type 1 thymidine kinase (tk) toxin gene under the control of Tat responsive region (TAR). The tk gene product, conditionally lethal to the cell, is toxic to mammalian cells only in the presence of nucleoside analogs, such as ganciclovir (Ventakash et al., 1990, Proc. Natl. Acad. Sci. USA 87: 8746–8750; Brady et al., 1994, Proc. Natl. Acad. Sci. USA 91: 365–369; WO 90/07936, Jul. 26, 1990; A similar approach has been attempted using the diphtheria toxin gene under the control of cis-acting HIV regulatory sequences (U.S. Pat. No. 5,306,631, issued Apr. 26, 1994). Other groups have utilized replication incompetent mutants of HIV which have the potential to express an inhibitory gene product in the presence of HIV tat (WO 94,16060, Jul. 21, 1994).

Recombinant retroviral and adeno-associated viral based vectors have been engineered to express foreign gene products in host cells for the purpose of treating viral and cancerous diseases (WO 91/02805, Mar. 7, 1991; WO 91/18088, Nov. 28, 1991). Retroviral vectors have been further designed to be capable of expressing multiple protein translation products from a single polycistronic mRNA, by using internal ribosome entry sites in place of an internal promoter (WO 93/03143, Feb. 18, 1993).

Recombinant parvoviral vectors have been engineered for tumor specific expression of interleukin genes (Russell et al., J. Virol. 66: 2821–2828). Parvoviral vectors have also been engineered to produce parvoviral antigens and to also produce empty, non-infectious parvovirus capsids in order to deliver genetic information (WO 90/05538, May 31, 1990).

Other advances in gene therapy involve recombinant mammalian stem cells which express heterologous gene products to degrade metabolites in the treatment of metabolite disorders (WO 88/08450, Nov. 3, 1988).

2.2. THE HUMAN IMMUNODEFICIENCY VIRUS

HIV has been implicated as the primary cause of AIDS (Barre-Sinoussi et al., 1983, Science 220:868–870; Gallo et al., 1984, Science 224:500–503). Infection of human CD-4+ T-lymphocytes with an HIV virus leads to depletion of this cell population, resulting in an immunodeficient state, and eventually opportunistic infections, neurological dysfunctions, neoplastic growth, and ultimately death. There are at least two distinct types of HIV: HIV-1 (Barre-Sinoussi et al., 1983, Science 220:868–870; Gallo et al., 1984, Science 224:500–503) and HIV-2 (Clavel et al., 1986, Science 233:343–346; Guyader et al., 1987, Nature 326:662– 669). A large amount of genetic heterogeneity exists within each of these HIV subtypes.

HIV is a member of the lentivirus family of retroviruses (Teich et al., 1984, RNA Tumor Viruses, Weiss et al., eds., CSH-Press, pp. 949–956). Retroviruses are small enveloped viruses that contain a diploid, single-stranded RNA genome, and replicate via a DNA intermediate produced by a virally-encoded reverse transcriptase, an RNA-dependent DNA polymerase (Varmus, 1988, Science 240:1427–1439). Other retroviruses include, for example, oncogenic viruses such as human T-cell leukemia viruses (HTLV-I and -II), and feline leukemia virus.

HIV is specifically targeted to CD-4+cells because the CD-4 cell surface protein acts as the cellular receptor for the HIV-1 virus (Dalgleish et al., 1984, Nature 312:763–767; Klatzmann et al., 1984, Nature 312:767–768; Maddon et al., 1986, Cell 47:333–348). Viral entry into cells is dependent upon viral gp120 binding to the cellular CD-4 receptor molecules (McDougal et al., 1986, Science 231:382–385; Maddon, P. J. et al., 1986, Cell 47:333–348).

After infection, the HIV transactivator protein, Tat, plays a central role in the subsequent viral gene regulation and replication (Cullen, 1986, Cell 46:973; Sarvey and Rossi, 1993, AIDS Res. Hum. Retroviruses 9:483). The Tat protein is a small diffusible protein encoded by the viral genome, which markedly enhances the expression of viral genes and the production of new infectious virions at transcriptional or post-transcriptional steps. The Tat protein exerts its effects by interacting with the short nucleotide sequence designated TAR, which is located within the 5' LTR region of viral mRNA transcripts.

2.3. HIV TREATMENT

HIV infection is pandemic and HIV-associated diseases represent a major health problem world-wide. Although considerable efforts have been devoted to the design of effective therapeutics, there is no curative anti-retroviral drugs against AIDS. In an attempt to develop such drugs, several stages of the HIV life cycle have been considered as targets for therapeutic intervention (Mitsuya et al., 1991, FASEB J. 5:2369–2381). For example, virally encoded reverse transcriptase has been one focus of drug development. A number of reverse-transcriptase-targeted drugs, including 2',3'-dideoxynucleotide analogs such as AZT, ddI, ddc, and d4T have been shown to be active against HIV (Mitsuya et al., 1991, Science 249:1533–1544). While beneficial, these nucleotide analogs are not curative, probably due to the rapid appearance of drug resistant HIV mutants (Lander et al., 1989, Science 243:1731–1734). In addition, the drugs often exhibit non-specific toxic side effects, such as bone marrow suppression, vomiting, and liver function abnormalities.

Another stage of HIV life cycle that has been targeted is viral entry into the cells, the earliest stage of HIV infection. Here, the focus has thus been on the use of recombinant soluble CD-4 to inhibit infection of CD-4+T-cells by some HIV-1 strains (Smith et al., 1987, Science 238:1704–1707). Certain primary HIV-1 isolates, however, are relatively less sensitive to inhibition by recombinant CD-4 (Daar et al., 1990, Proc. Natl. Acad. Sci. USA 87:6574–6579). In addition, recombinant soluble CD-4 clinical trials have produced inconclusive results (Schooley et al., 1990, Ann. Int. Med. 112:247–253; Kahn et al., 1990, Ann. Int. Med. 112:254–261; Yarchoan et al., 1989, Proc. Vth Int. Conf. on AIDS, p. 564, MCP 137).

The later stages of HIV replication, which involve crucial virus-specific secondary processing of certain viral proteins, have also been suggested as possible anti-HIV drug targets. Late stage processing is dependent on the activity of a viral protease, and drugs have been developed to inhibit this protease (Erickson, 1990, Science 249:527–533). However, the clinical utility of these candidate drugs is still in question.

Although a great deal of efforts are being directed to the design and testing of diverse classes of anti-retroviral therapeutics, a truly effective, non-toxic treatment for AIDS is still needed.

2.4. PARVOVIRUS

The parvoviruses are a family of small, non-enveloped, icosahedral animal viruses which contain a single-stranded DNA genome of about 5 kilobases (kb). They exhibit several characteristics which recommend them as viral vectors for the delivery of therapeutic protein molecules into target cells. Adeno-associated viruses (AAV) are members of the Dependovirus subgroup of parvoviruses, and they require an adenovirus or herpes virus helper to undergo productive infection. In the absence of helper effect, the AAV genome integrates efficiently into the host DNA, possibly in the absence of cellular DNA synthesis, and this has led to their use as integrative vectors (Muzyczka, 1992, Curr. Top. Microbiol. Immunol., 158:97–129; Xiao et al, 1993, Advanced Drug Delivery Reviews, 12:201–215). Indeed, some of these vectors hold out the possibility of high efficiency site specific integration, since they preferentially integrate at a specific location on human chromosome 19 (Muzyczka, 1992, Curr. Top. Microbiol. Immunol., 158:97–129; Xiao et al, 1993, Advanced Drug Delivery Reviews, 12:201–215; Kotin et al., 1990, Proc. Natl. Acad. Sci. U.S.A., 87:2211–5; Kotin et al., 1991, Genomics, 10:831–4; Kotin et al., 1992, EMBO J., 11:5071–8).

In contrast, the autonomous or helper-virus independent subgroup of rodent parvoviruses, to which minute virus of mice (MVM) belongs, have yet to be shown to integrate into the host cell genome, although they persist for long periods of time in the infected host (Tattersall et al., 1986, Viral and Mycoplasma Infections of Laboratory Rodents: Effect on Biomedical Research, p. 305–348; Jacoby et al., 1991, Archives of Virology 117:193–205). In general, they require their host cells to be of a particular differentiated phenotype and to actively traverse the S-phase of the cell cycle in order to establish a productive infectious cycle. Although tissue tropism is mediated by the coat protein of the virus, it can operate at various levels both before and after cell penetration. The parvoviruses often undergo an abortive infection, expressing their early genes in cell types which ultimately do not succamb to full scale virus production.

The parvovirus virion has a relatively simple structure composed of only three related proteins and a linear, single-stranded DNA molecule. The particle has icosahedral symmetry and a diameter of 18 to 26 nm. Approximately 80% of the mass is protein and the remainder is DNA. Possibly as a consequence of its structural simplicity, the virion is extremely resistant to inactivation. The virus is stable between pH 3 and 9 and at 56° C. for 60 minutes.

The genetic organization of MVM is depicted in FIG. 1. One of the first gene products to be expressed after infection is the 83 kd major non-structural protein NS1, a nuclear phosphoprotein which is intimately involved in viral DNA replication. Soon after infection of permissive cells, trans-activation of expression from the P38 promoter occurs. Directed mutagenesis of sequences coding for NS1, and for NS2, a set of 24 kd, transiently-expressed, predominantly cytoplasmic phosphoproteins, has shown that only the NS1 polypeptide is required for P38 promoter transactivation (Doerig et al., 1988, J. Gen. Viol., 69:2563–2573). Site-specific mutagenesis of the NS2 coding region has revealed that these proteins are not essential for productive infection of some cell types, notably SV40-transformed human fibroblasts.

The coat protein gene of MVM produces two primary translation products, VP1 and VP2, with molecular weights of 83 kd and 64 kd, respectively (Tattersall et al., 1976, J. Virol. 20:273–289). The latter of these is the most abundant, and comprises the C-terminal three-quarters of VP1 (Tattersall et al., 1977, J. Mol. Biol., 111:375–94). VP2 can also be processed to VP3, in full virions only, by proteolytic cleavage of approximately 30 amino acids from its N-terminus. The crystal structure of a closely related virus, canine parvovirus reveals that the icosahedral shell of the virion comprises sixty copies of the polypeptide chain common to VP1, VP2 and VP3 (Wu et al., 1993, J. Mol. Biol., 233:231–44; Agbandje et al., 1993, Proteins: Structure, Function & Genetics, 16:155–71; Tsao et al., 1991, Science, 251:1456–64). No structural information has been obtained for the VP1-specific region, which is highly basic and probably interacts with the viral DNA (Tattersall et al., 1977, J. Mol. Biol., 111:375–94).

3. SUMMARY OF THE INVENTION

The present invention relates to chimeric viruses which can be used to treat pathological or disease conditions, including but not limited to infectious diseases and cancers. The chimeric viruses are designed so that their replication is regulated by a transactivation signal produced by the diseased host cells. The chimeric viruses of the invention are engineered from parental strains that are infectious and cytocidal to the target host cell—those viruses that display a tropism, either natural or engineered, for the target host cell may advantageously be used. The parental virus is altered so that one or more regulatory regions which control the expression of early viral genes involved in viral replication contain a transactivator responsive element (TRE) specific for the transactivating signal produced in the disease of interest. Chimeric viral infection of a diseased host cell that produces the transactivation signal will result in activation of the chimeric virus which kills the diseased host cell; i.e., the early viral genes involved in viral replication should be expressed at sufficiently high levels in response to the transactivating signal, in order to shift the chimeric virus from a "latent" state where the virus has little or no physiological effect on the host cell to a "cytocidal" state. Activation of the chimeric viruses results in expression from the chimeric viral genome, but not necessarily the production of infectious progeny virions. The chimeric cytocidal virus will infect, but not express its genes in or kill normal target cells that do not produce the transactivation signal. However, in the absence of the transactivating signal, activation of the chimeric cytocidal virus may be "leaky" provided it does not result insignificant killing of non-diseased cells.

The chimeric virus can be further modified to produce a cytocidal-antagonist or non-cytocidal-antagonist chimeric virus. In cytocidal-antagonist viruses, a region of the chimeric viral genome that is non-essential or complementable for viral replication is modified to contain an additional sequence encoding a product that inhibits the expression or activity of a gene product involved in the disease pathway, or one which inhibits replication of the infectious pathogen. Such cytocidal-antagonist chimeric viruses will inhibit replication and spread of the pathogen and kill the affected host cell.

Non-cytocidal-antagonist chimeric viruses are engineered to contain a negative feedback loop that limits both production of the pathogen and replication of the chimeric virus. In such cases, a region of the chimeric viral genome that is non-essential or complementable for replication is modified to contain a sequence encoding a product that inhibits the production or activity of the transactivation signal produced by the diseased host cell. Such non-cytocidal-antagonist chimeric viruses will inhibit the expression or activity of the transactivator, inhibit replication of the pathogen, and inhibit replication of the chimeric virus itself so that the infected host cell will survive provided the pathogen is suppressed.

The engineered chimeric viruses can be rescued and propagated in host cell/vector systems that supply the viral functions required for replication in trans e.g., the host cell/vector system must supply the transactivator function in order to produce the chimeric cytocidal viruses in quantity. In addition any essential functions deleted from the cytocidal-antagonist or non-cytocidal-antagonist chimeric virus must also be provided in trans in order to produce infectious viral stocks for use in treating disease.

The invention is illustrated for the treatment of HIV infection using a murine parvovirus. The present invention is based, in part, on the Applicants' discovery that virions of the murine lymphotropic MVMI are capable of delivering their single-stranded DNA genome efficiently into cultured human lymphocytes. The viral non-structural genes are subsequently expressed at high levels, which leads to death of the cells without significant release of infectious MVM. However, when the early promoter region of this virus is replaced with another virus regulatory sequence, such as the HIV-1 long terminal repeat (LTR), the chimeric MVM can be recovered as live, replication-competent virus by transfection into non T-cell lines which express tat constitutively. Remarkably, this recovered chimeric virus is restricted in its growth and cell killing ability to tat-expressing cells of both T- and non T-cell origin. In contrast, the chimeric virus does not replicate in non-tat expressing cells (such as normal T cells) to an extent which results in significant cell death. A wide variety of uses are encompassed by the present invention, including but not limited to, suppression of infection by HIV, HBV and HTLV.

4. BRIEF DESCRIPTION OF THE DRAWINGS

FIG. 1. The coding strategy of the MVM genome. The positions of the two promoters, P4 and P38, within the negative strand viral genome with its terminal hairpins are displayed above the mRNA splicing strategy. The shaded boxes indicate the reading frame which encodes each segment of viral polypeptide.

FIGS. 2A–2D. Schematic diagram of the HIV LTR and the MVM P4 region and the chimeric promoter present in the MVMπ-Tar 1 and 2 viruses. FIG. 2B: MVM sequences in the P4 promoter region. The ATG underlined is the start codon for the NS1/2 gene. FIG. 2C: HIV sequences in the LTR promoter region. Sequences inserted into MVM in the chimera are in bold. FIG. 2D: Sequences in the chimeric promoter region. HIV-derived sequences are in bold. Lower case nucleotides are those mutated in the chimera to produce the unique KpnI site.

Figure 3:
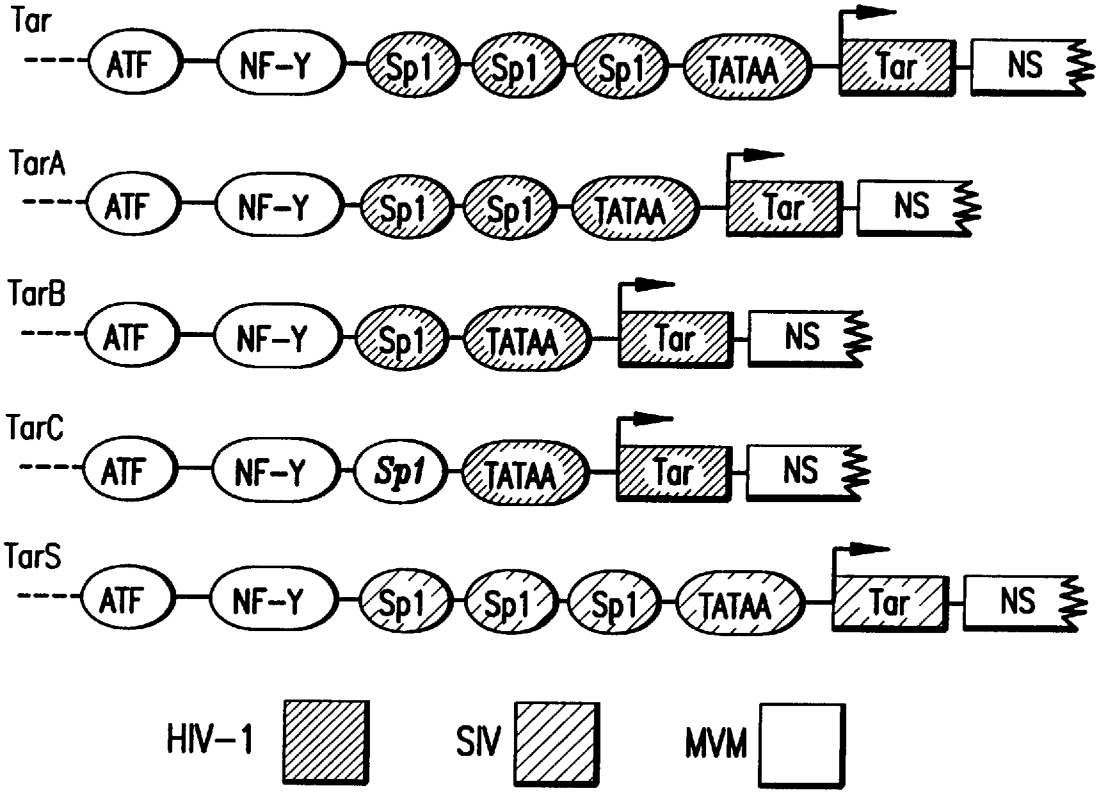

FIG. 3. Schematic diagram of additional chimeric promoters, incorporating different elements of the MVM P4 promoter and the HIV-1 or SIV promoter. Tar-A, Tar-B and Tar-C differ by the sequential removal of HIV-1 Sp1 binding sites, and the remaining, most promoter proximal HIV-1 Sp1 site being replaced in Tar-C by the equivalently-located, but unique Spl site of MVM.

Figure 4:
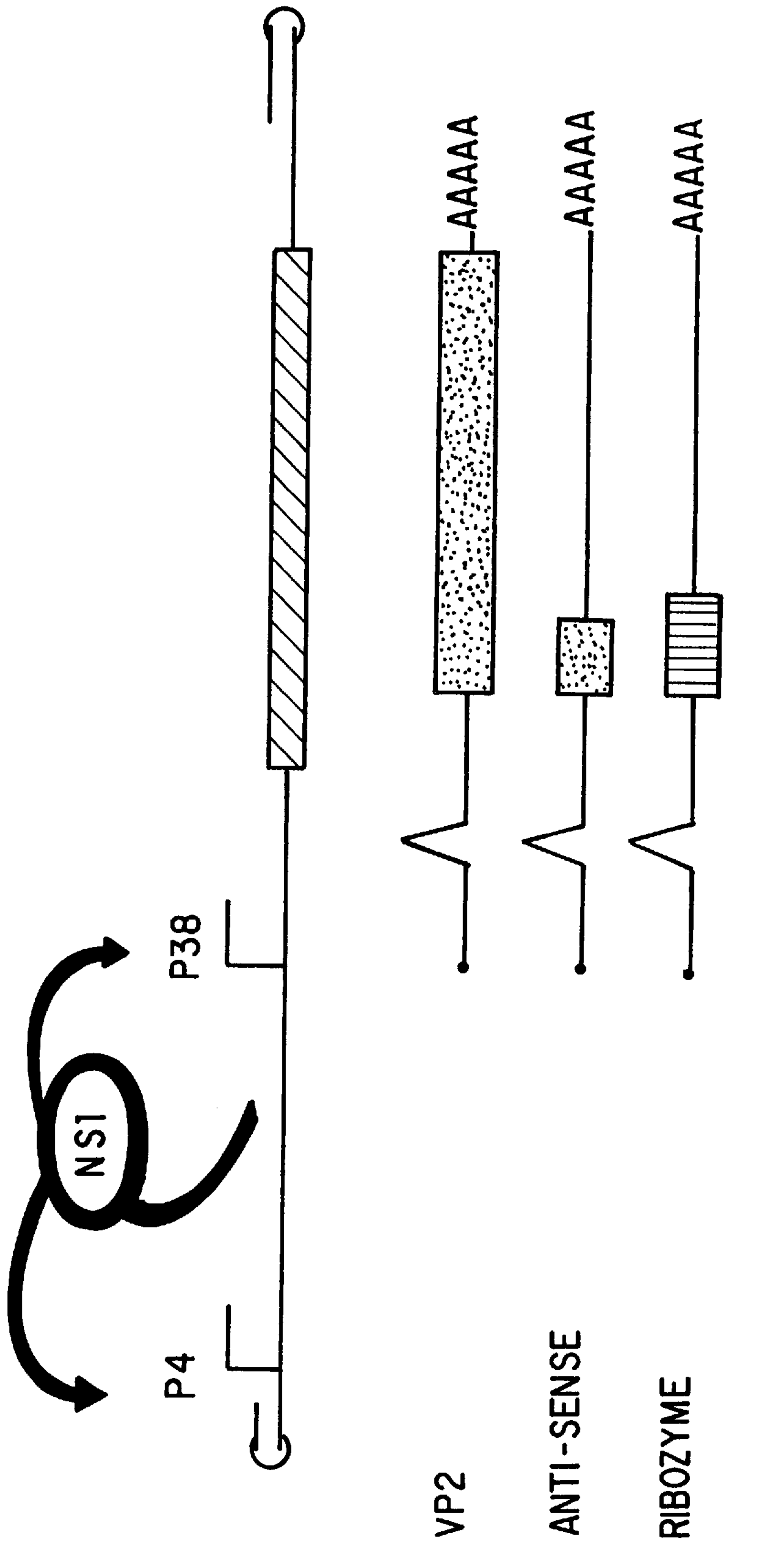

FIG. 4. Schematic diagram of the cloning vehicle for construction of the non-cytocidal-antagonist chimeric vectors. The modified VP2 gene segment is the recipient for the target virus antagonist sequences.

Figure 5:
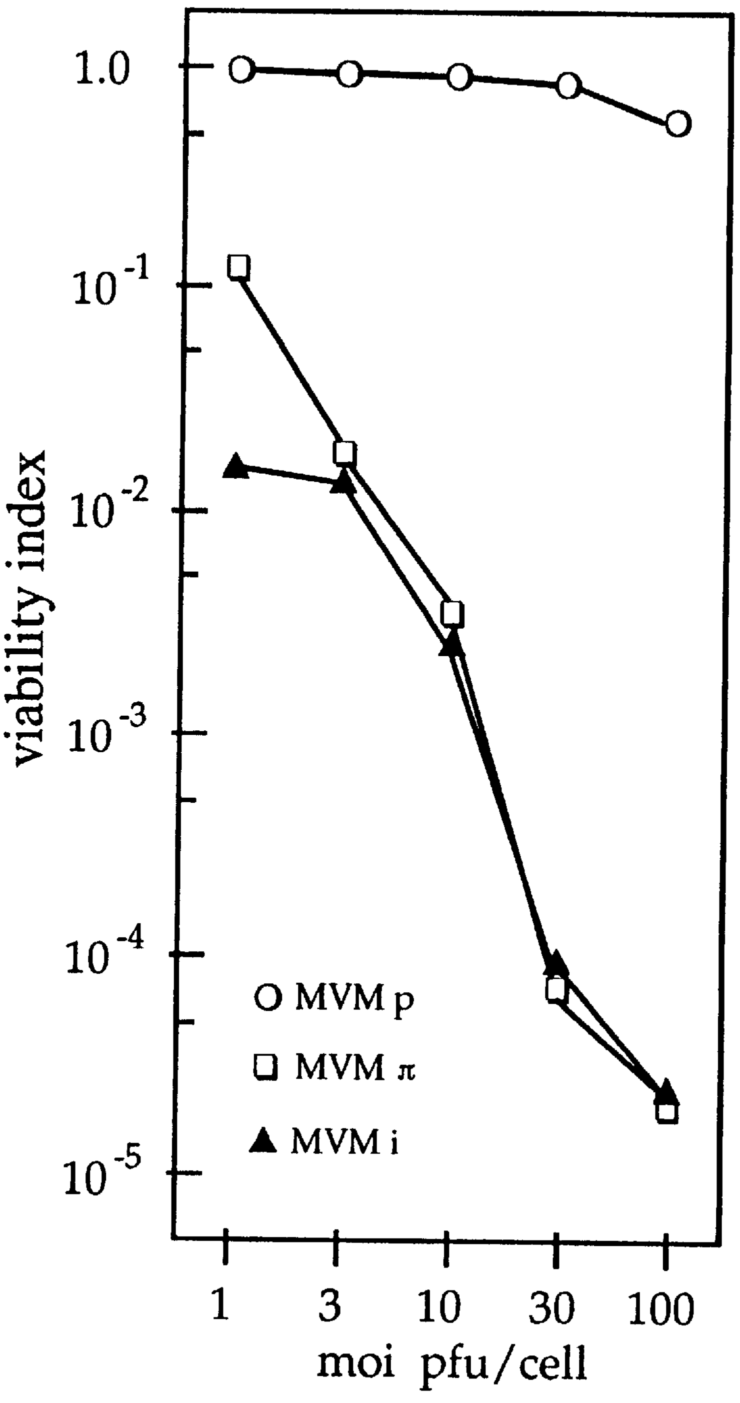

FIG. 5. Survival of human H9 cells infected with MVM, 5 days post infection. The lymphotropic murine parvovirus, MVMi, binds to and replicates in human T-cell lines resulting in cell death, whereas even high multiplicities of MVMP, the prototype, fibrotropic strain, have little effect on H9 survival.

Figure 6:
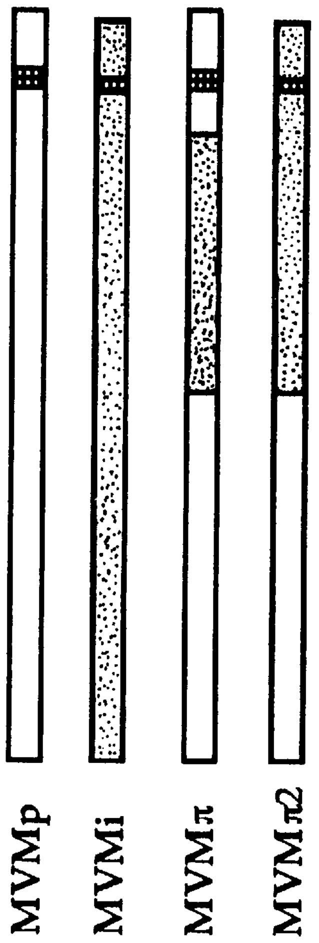

FIG. 6. Schematic representation of the construction of the recombinant viruses MVMV and MVMπ-2, in which most of the capsid gene of MVMi has been transferred into the MVMp background.

Figure 7:
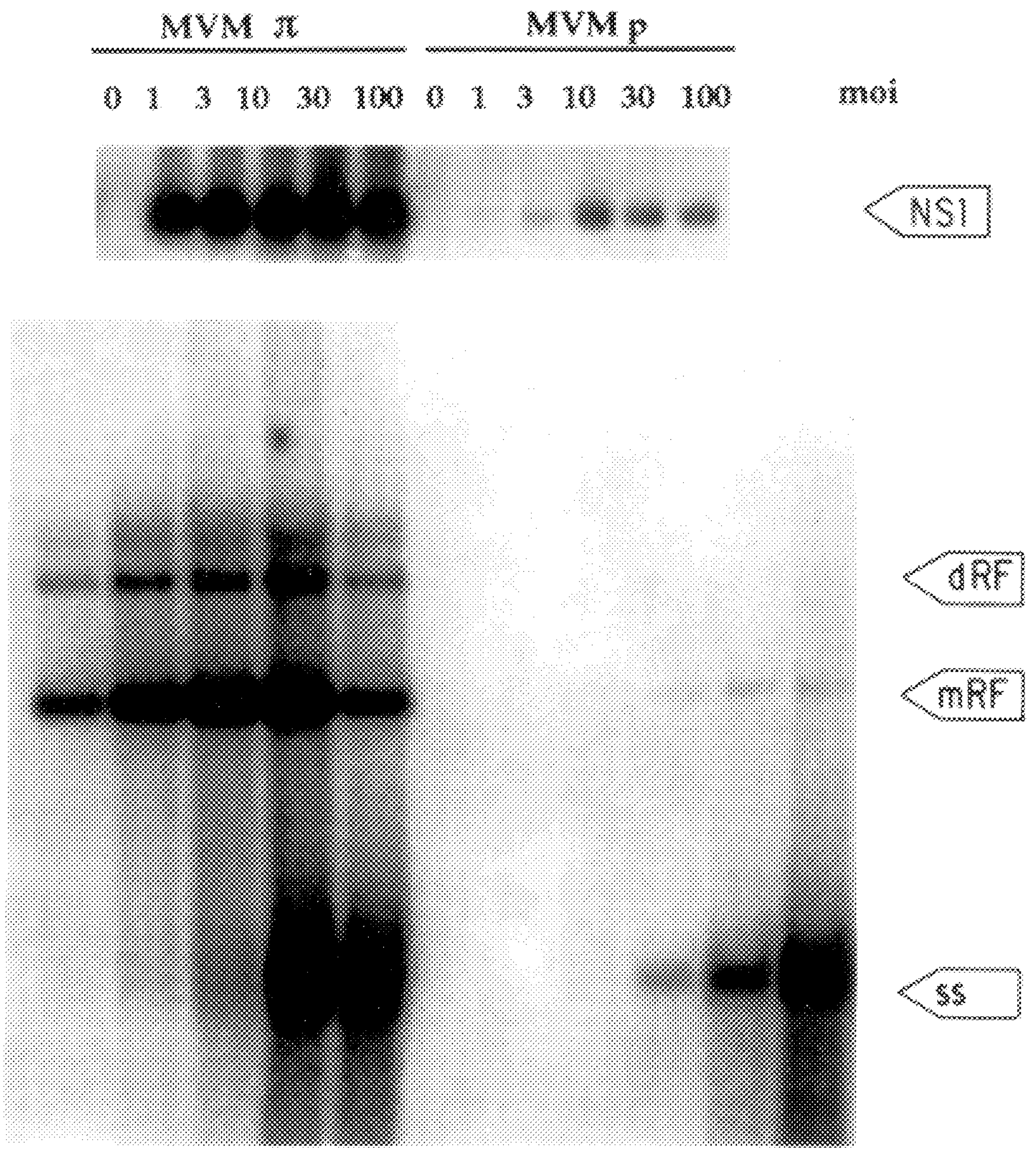

FIG. 7. MVM expression and replication in H9 cells. The recombinant MVMπ viral vector abundantly expresses its major non-structural protein, NS1, in human T cell lines, as detected by Western blot in the top panel, using a specific anti-NS1 fusion antibody. Very little NS1 is detected in MVMp-infected H9 cells. Analysis of viral DNA replication, as demonstrated by Southern blot in the lower panel, gives a very similar pattern.

Figure 8A:
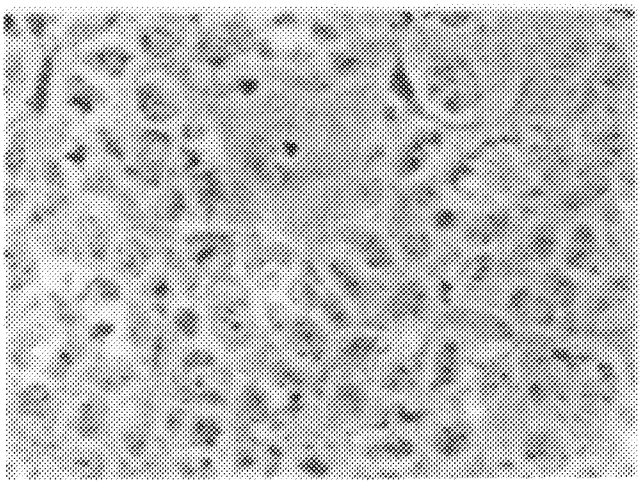
Figure 8B:
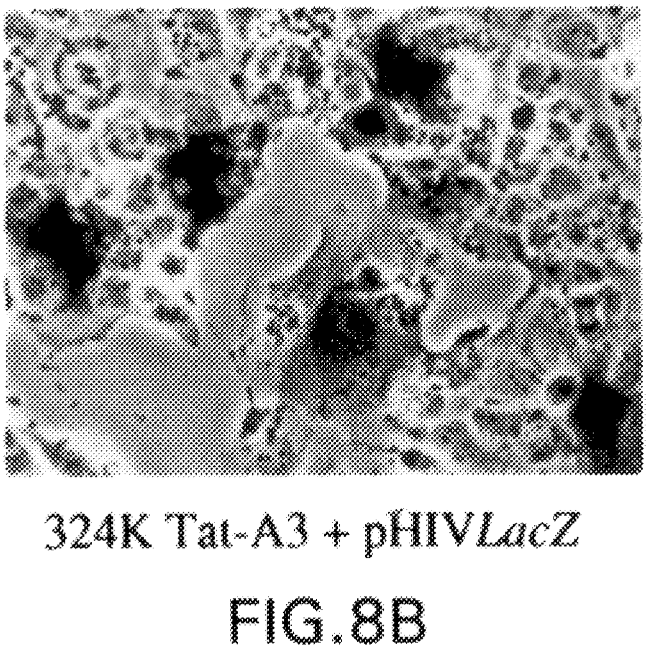

FIGS. 8A–8B. The G418 resistant cell lines 324K Tat-A3, (FIG. 8B) and its parent 324K B6-S13, (FIG. 8A) are evaluated by lipofectAMINE-mediated transfection of pHIV-LacZ, followed by staining 60 hours later for β-galactosidase activity.

Figure 9:
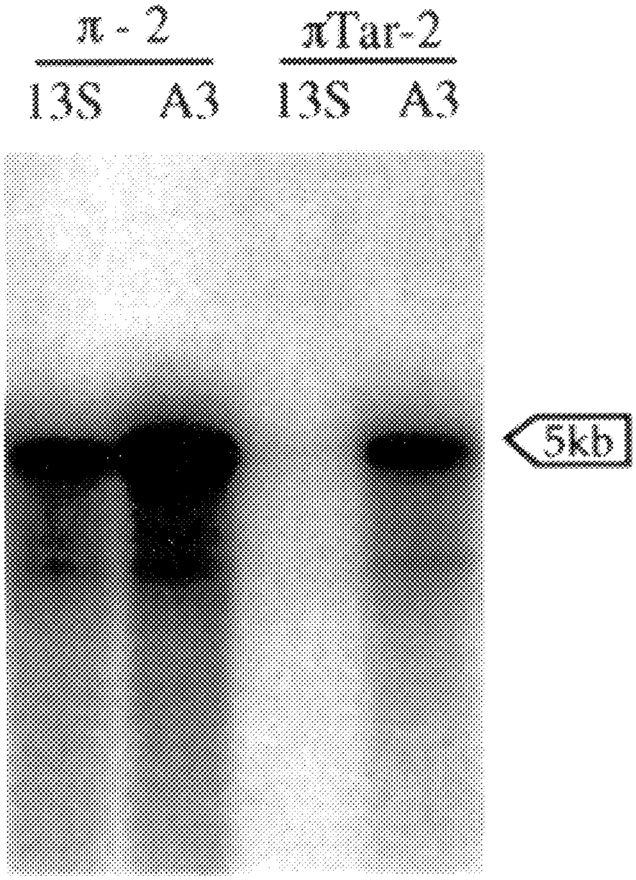

FIG. 9. Southern blot of an alkaline gel of micrococcal nuclease-treated extracts from transfected 324K B6-13S or Tat-A3 cells, demonstrating that virion accumulation for MVMπTar-2 depends upon tat expression in the host cell.

Figure 10:
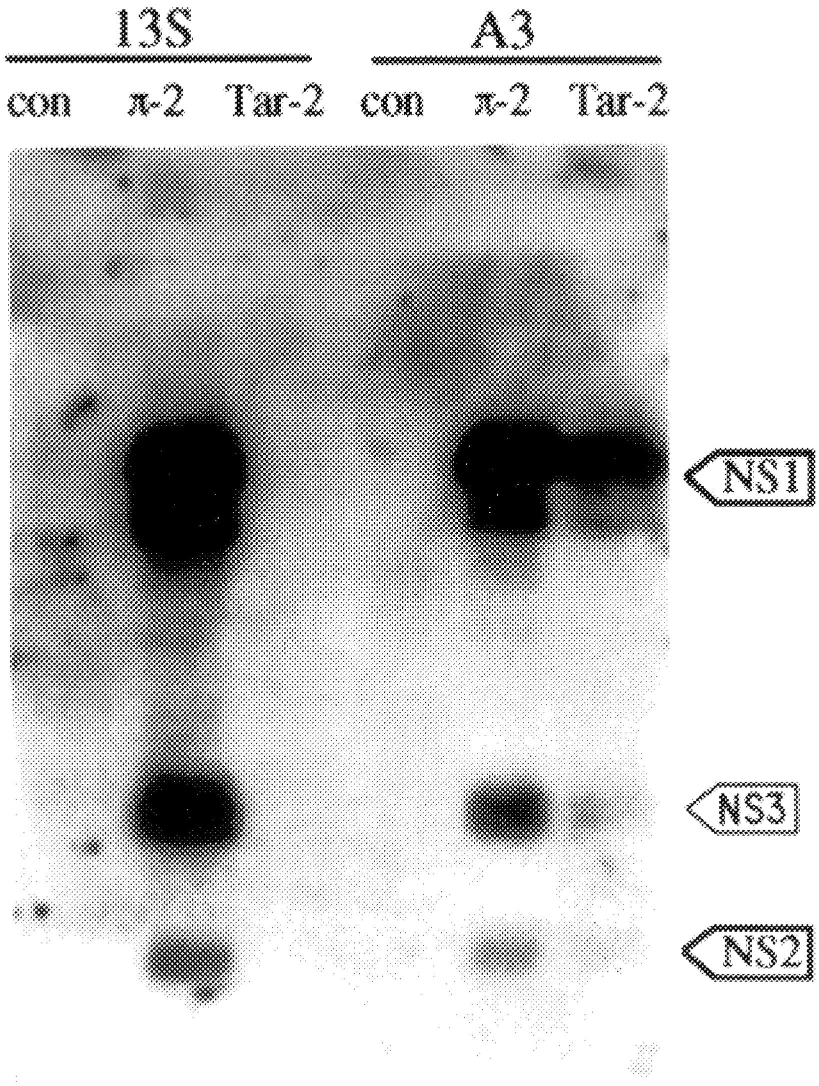

FIG. 10. Western blot analyses of NS gene expression demonstrate that gene expression is somewhat lower for MVMπTar-2, compared to MVMπ-2, in Tat-A3 cells.

Figure 11:
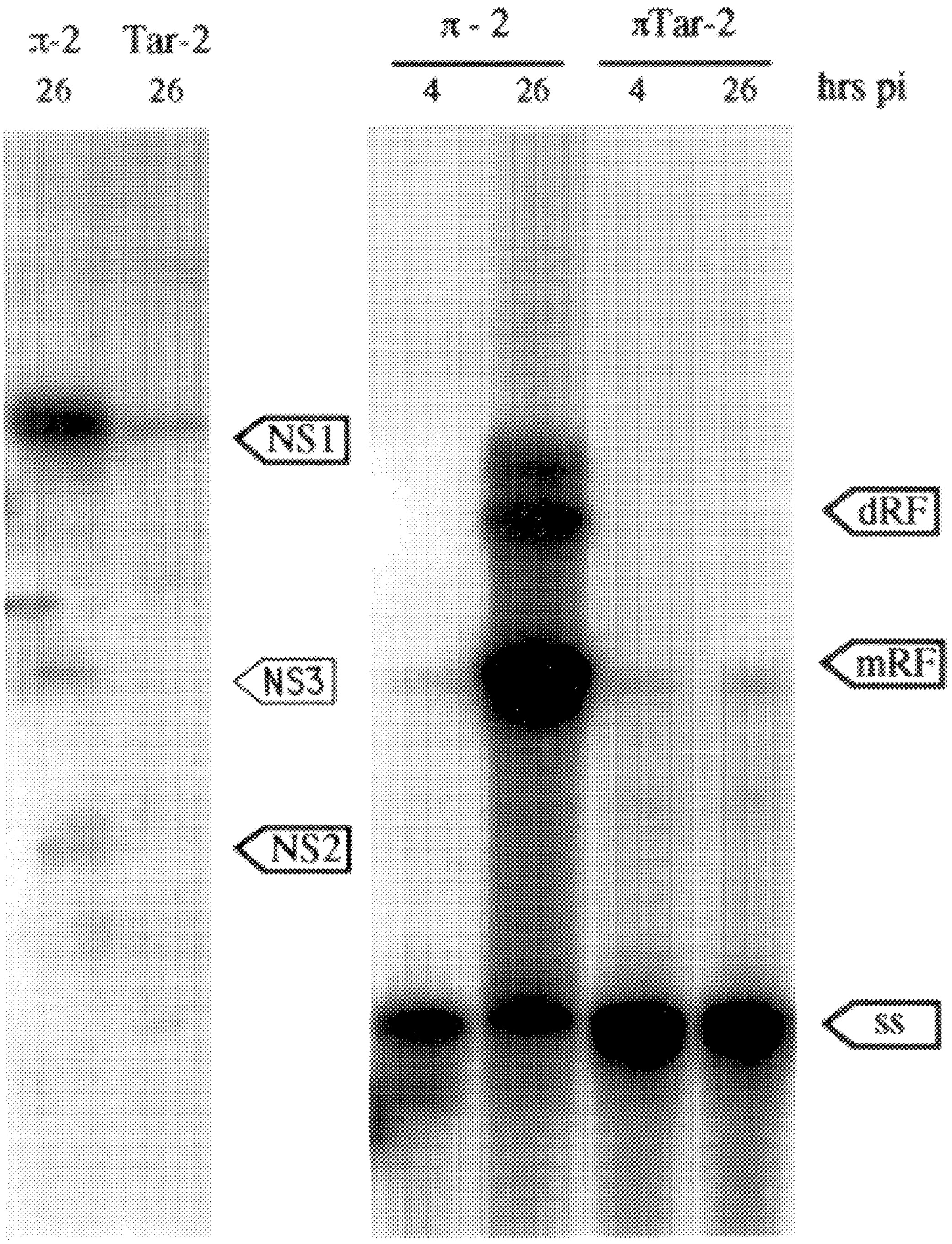

FIG. 11. Western blot of NS1 gene expression and Southern blot of DNA replication in H9 cells infected with MVMπTar-2 or MVMπ-2.

Figure 12:
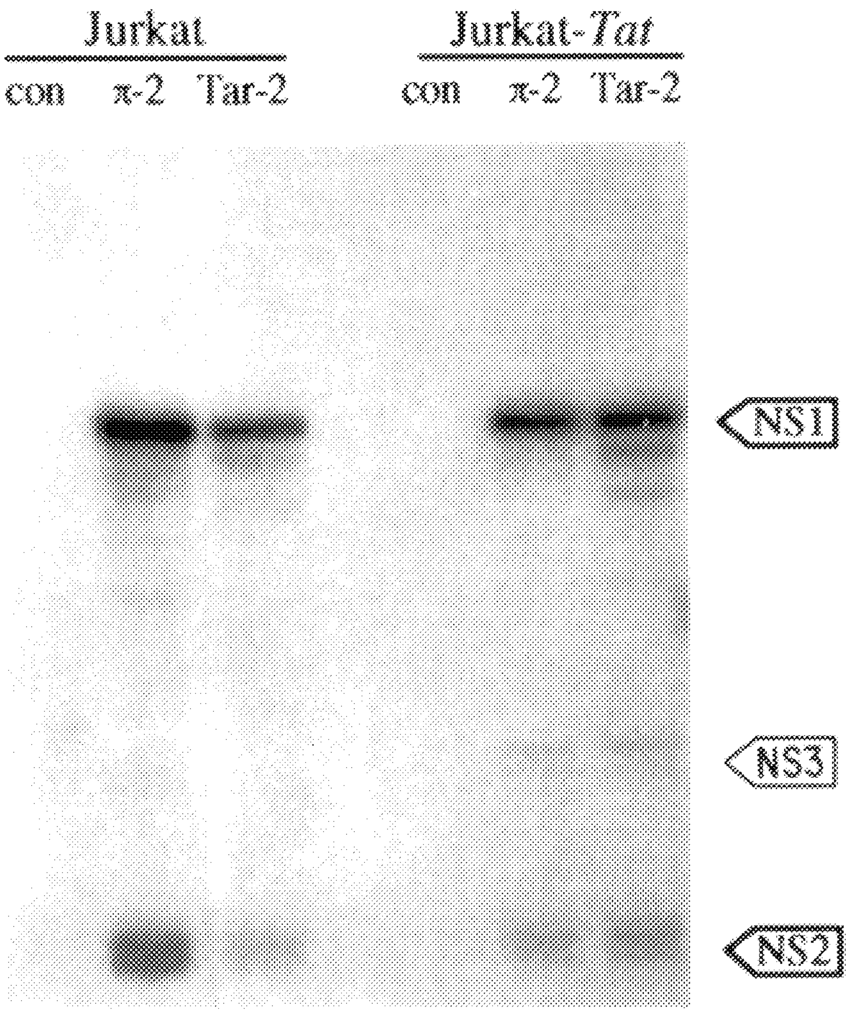

FIG. 12. Western blot analysis of NS1 gene expression in Jurkat cells infected with MVMπ-2 and MVMπTar-2, in the presence or absence of tat.

5. DETAILED DESCRIPTION OF THE INVENTION

Chimeric viruses that can be used to treat pathological or disease conditions, including but not limited to infectious diseases and cancers, are described. The chimeric viruses of the invention are engineered by modifying viruses capable of infecting host cells that are targets for the disease or pathogen, so that replication of the resulting chimeric virus is regulated by appropriate transactivation signals produced by the diseased host cells. Activation of the chimeric viruses results in expression from the chimeric viral genome, but not necessarily the production of infectious progeny virions. This is accomplished by modifying a virus that is capable of infecting the host cell, so that the region of the virus responsible for initiating its infectious process is chimeric, containing a regulatory element responsive to the transactivating signal produced by the diseased host cell. This engrafted regulatory element will be referred to herein as the transactivator-responsive element, or "TRE".

At least three types of chimeric viruses can be designed and engineered in accordance with the invention: cytocidal, cytocidal-antagonist, or non-cytocidal-antagonist. Replication of cytocidal chimeric viruses in response to the transactivating factor produced by the diseased host cell will result in cell death, and therefore will limit the expansion of the diseased cells and/or the further transmission of the pathological infectious agent. The chimeric virus will not initiate its replicative cycle in normal or non-diseased host cells that do not express the transactivating signal; therefore, normal cells infected by the cytocidal chimeric virus will be spared. Stocks of the resulting chimeric virus can be produced using host cells and/or vectors that supply the transactivator function in trans.

To produce cytocidal-antagonist viruses, the cytocidal chimeric virus can be further engineered so that a region of the chimeric viral genome that is non-essential or complementable for viral replication is modified to contain an additional sequence encoding a product that inhibits the expression or activity of a different gene product involved in the disease pathway, or one which inhibits replication of the infectious pathogen. Such cytocidal-antagonist chimeric viruses will both inhibit replication and spread of the pathogen, and kill the infected host cells.

In yet another embodiment, the cytocidal virus can be engineered so that it is non-cytocidal-antagonist, or self-limiting, by designing a negative feedback loop that limits both production of the pathogen and expression of the chimeric virus. In particular, the cytocidal chimeric virus can be further engineered so that a region of the chimeric viral genome which is non-essential or complementable for viral replication is modified to contain a sequence encoding a product that inhibits the production or activity of the transactivation signal produced by the diseased host cell. Decreased expression of the transactivator will inhibit both the replication of the pathogenic infectious agent and the expression and/or replication of the chimeric virus, thus allowing the host cell to live while the undesirable effects of the pathogen are suppressed.

The invention is illustrated by way of working examples which describe the construction of a parvovirus useful for the treatment of HIV infection. In particular, a murine parvovirus which infects human T cells was modified by replacing the viral regulatory region with an HIV-tat responsive element. The resulting chimeric parvovirus efficiently initiates infection in human cells that express HIV-tat, and leads to cell death due to expression of the parvoviral non-structural gene products (NS) that are toxic to the host cell. The chimeric parvovirus does not replicate in normal host cells that do not express HIV-tat, and does not result in significant killing of such cells.

The chimeric parvovirus can be further engineered as a cytocidal-antagonist or non-cytocidal-antagonist chimeric virus for the treatment of HIV-infection. For example, the parvoviral gene for coat protein can be rendered non-essential for growth by supplying the capsid gene products in trans. Thus the capsid genes in the chimeric parvovirus can be replaced with a sequence that encodes a product which inhibits HIV replication. Stocks of the resulting cytocidal-antagonist or non-cytocidal-antagonist chimeric virus can be produced using host cells and/or vectors that supply both the parvoviral coat protein and the HIV-tat protein in trans.

An important advantage of placement of such antagonist cassettes in the parvoviral capsid gene is that the transcript and/or proteins they encode are expressed at very high levels in response to the pathogen transactivator. This is due to transactivation of the capsid P38 promoter by the NS1 gene product, which has itself been placed under the control of the TRE of the pathogen. Alternatively, antagonist molecules that work as short transcripts, such as antisense, ribozymes, etc., can be engineered into the small intron common to most parvoviral mRNAs, and expressed as released, free intron RNA upon activation. When placed in this position the chimeric virus may retain its replicative competence, and not require the complementation strategy of providing capsid proteins in trans, described for the capsid gene replacement viruses. This strategy also benefits from the high level expression generated from the P38 promoter when it is transactivated by viral NS1.

Any sequence that encodes a gene product or transcript that works to inhibit HIV-replication can be engineered into such a non-essential or complementable region of the chimeric parvoviral genome to yield the cytocidal-antagonist chimeric virus—i.e., a virus that inhibits HIV-replication and kills the infected host cell. For example, dominant-negative mutant forms of HIV-env or HIV-rev can be engineered into the chimeric parvovirus. The expression of such defective mutant HIV-proteins by the host cell will inhibit the propagation of HIV. Alternatively, soluble CD4 or a CD4 fusion protein that is retained by the endoplasmic reticulum and Golgi apparatus can be engineered into the chimeric parvovirus. Expression of such mutant forms of the CD4 receptor by the host cell will inhibit the release of HIV virions. Alternatively, an HIV-protease inhibitor can be engineered into the chimeric parvovirus so that propagation of HIV is inhibited.

In yet another approach, sequences encoding “decoy” RNAs, antisense or ribozymes that prevent or inhibit translation of any HIV transcript important for HIV replication can be engineered into a non-essential or complementable region of the chimeric parvovirus. Alternatively, a sequence encoding a transcript that forms a triple helix with a regulatory region of an HIV-gene important for HIV replication can be engineered into a non-essential or complementable region of the chimeric parvovirus to prevent transcription of mRNAs important for HIV replication. Such chimeric parvoviruses will both “shut down” HIV replication (due to the anti-HIV sequence engineered into the non-essential or complementable region) and kill the HIV-infected cell (due to the expression of toxic parvoviral NS gene products).

In another embodiment, any sequence that encodes a gene product or transcript that inhibits HIV-tat production or activity can be engineered into a non-essential or complementable region of the chimeric parvoviral genome to yield a non-cytocidal-antagonist chimeric virus—i.e., one that operates by eliciting a negative feedback loop by which replication of both HIV and the chimeric virus are shut down, and the host cell survives. For example, the parvoviral gene for coat protein can be replaced with any of the following sequences, alone or in combination: a sequence encoding an antisense molecule that is complementary to, and blocks translation of, HIV-tat mRNA; a ribozyme that cleaves the HIV-tat mRNA and prevents its translation; a transcript that forms a triple helix with the HIV-tat regulatory region; and thus prevents transcription of HIV-tat; provided that each is designed to interfere with tat synthesis in HIV-infected cells but not the producer cell line in which stocks of the chimeric virus are prepared. When this type of chimeric parvovirus is used to treat HIV-infected cells, the chimeric virus will not only replicate, but it will express the HIV-tat inhibitory sequence. Inhibition of HIV-tat activity or expression in the infected host cell will, in turn, inhibit replication of both HIV and the chimeric virus in the host cell. As a result, the cells infected with chimeric virus should survive while HIV replication will be suppressed.

For clarity of discussion, the different aspects of the invention are described using the chimeric parvoviral system for the treatment of HIV infection. However, the principles may be analogously applied to other disease targets that involve a transactivation signal, including but not limited to hepatocellular diseases, such as HBV infection, retroviral diseases such as leukemias caused by HTLV-1 infection, or cancers for which oncogenes having transactivating functions have been identified, e.g., cancers in which the myc oncogene is over-expressed such as Burkitt’s lymphoma and glial carcinomas. Likewise, the chimeric viruses of the invention are not limited to chimeric parvoviruses. Any virus that demonstrates an appropriate tropism (either naturally or engineered) for the host cells which are targets for the disease can be used; e.g., viruses which can be used as the parental virus for generating the chimeric viruses of the invention include but are not limited to parvoviruses, retroviruses, adeno-viruses, adeno-associated viruses, vaccinia viruses, herpes viruses, etc. For rescue of chimeric virus and production of chimeric virus stocks, the transactivation signal must be provided by a host cell/vector system in trans. Where the design of a chimeric virus involves the removal of a portion of the viral genome required for packaging, release and infectivity of progeny stains, such additional functions can be supplied in trans by the host cells and/or recombinant vectors used for the production of chimeric virus stock used in the present invention.

The invention may be divided into the following stages solely for the purpose of description and not by way of limitation: (a) identification of the viral regulatory sequences required for viral gene expression and replication, and genes non-essential for expression or replication as sites for insertion of foreign sequences; (b) construction of the recombinant chimeric viruses; (c) assays to test the effectiveness of the recombinant vectors in vitro and in vivo. These stages are described in more detail in the subsections below.

5.1. ENGINEERING THE CHIMERIC VIRUS

For the practice of the present invention, viruses which display a suitable tropism for the disease target cells, or which are genetically engineered to display a suitable tropism for the diseased target cells, are genetically engineered to contain chimeric regulatory regions that respond to specific transactivation signals produced by the diseased host cells.

The viruses which can be used for purposes of the invention include, but are not limited, to parvoviruses, retrovirus, adenovirus, adeno-associated virus, herpes virus, vaccinia virus, etc. The choice of virus will depend, in part, on the nature of the disease to be treated, taking into account the tropism of the virus (natural or engineered) for the host cells which are targets for the disease. The transactivator-responsive element, or TRE, that is engineered into the viral genome in order to construct the chimeric virus will also depend upon the disease to be treated. For example, retroviral LTRs which bind HIV-tat can be used as TREs for the construction of chimeric viruses useful for treating HIV-infection; HBEnI and HBEnII elements of HBV which are responsive to the HBX protein can be used as TREs for engineering chimeric viruses to treat HBV-infection; Tax responsive elements of HTLV can be used as TREs to engineer chimeric viruses responsive to Tax to treat HTLV-induced leukemias; Myc responsive elements can be used as TREs to engineer chimeric viruses to treat cancers which overexpress Myc, i.e. Burkitt’s lymphoma, small cell lung carcinomas, glial blastomas; ICP4 responsive elements of HSV can be used as TREs to engineer chimeric viruses to treat HSV; the HOX11 responsive element can be used as TREs for engineering chimeric viruses to treat T cell acute leukemias.

The parvovirus used in the working examples, described herein as illustrative of the invention, is a murine parvovirus (MVM) that surprisingly displays a natural tropism for human T cells. More surprisingly, replacement of the murine parvoviral transcriptional regulatory region with the TRE for HIV-tat generates a chimeric virus that infects human T cells, but which expresses its genes in and kills only those target T cells that express HIV-tat.

In the case of MVM, the major cis-acting functions that are essential for the first steps in viral DNA replication (Cotmore et al., 1992, Virology, 190:365–77; Cotmore et al., 1993, J. Viol., 67:1579–89) are found upstream of the P4, or "early" promoter. This is the initiating promoter for viral transcription, and its TATAA box is located 4 map units from the left-end of the MVM genome, at around nucleotide 150. The essential cis-acting function for the origin of DNA replication which resides in this region includes the ATF and NF-Y transcription factor binding sites shown in FIGS. 2A–2D and it extends to a point approximately halfway between this NF-Y site and the Sp1 binding site (Cotmore and Tattersall, 1994, EMBO J. 13:4145–4152). The ATF and NF-Y binding sites are integral components of the minimal origin of MVM DNA replication situated at the left-hand end (Cotmore and Tattersall, 1994, EMBO J. 13:4145–4152). The insertion of foreign DNA sequences, such as the TREs, just downstream of this region of the MVM genome allows for regulation of viral gene expression without disruption of other essential viral activities, such as DNA replication.

One of the first parvovirus gene products to be expressed after infection is the 83kd non-structural protein NS1. NS1 serves a number of separable functions in the viral life cycle. For example, it transactivates the late P38 promoter, and regulates expression from this otherwise quiescent promoter. Regulation of P38 by NS1 is normally used by the virus to produce copious quantities of its capsid proteins, VP1 and VP2. Therefore, inclusion of the NS1 gene sequences in the MVM vectors provides a considerable amplification step for therapeutic gene delivery. Enhanced transactivation of the VP1 and VP2 genes is important, since these nucleotide sequences serve as convenient sites for insertion of foreign DNA sequences in order to generate cytocidal-antagonist and non-cytocidal-antagonist chimeric viruses.

In addition to MVM, there are a number of distinct virus serotypes in the autonomous subgroup, which show similar genetic organization but different tissue and species specificities. Most of these viruses are currently available as infectious plasmid clones which can be manipulated in *E. coli,* and then rescued from the plasmid by transfection into appropriate mammalian cells in culture. Vectors capable of high level expression in human cells have already been constructed from the MVM genome by replacement of the capsid protein gene with the genes encoding the cytokines, interleukin 2 and 4. Since they lack an intact coat protein gene, these viral genomes are defective for packaging, and are induced to replicate by provision of viral structural proteins in trans from a co-transfected helper plasmid (Russell et al., 1992, J. Viol., 66:2821–8). These strains may be useful for the production of the cytocidal-antagonist or non-cytocidal-antagonist chimeric viruses of the invention.

Similar approaches may be applied to construct a chimeric retrovirus. For instance, human retroviruses which display a tropism for human T cells, e.g. HTLV-1 and HTLV-2 or animal retroviruses which display a tropism for human lymphocytes, e.g., Bovine leukemia virus, Moloney murine leukemia virus, Rous-associated virus, and feline leukemia virus, may be used to target HIV-infected cells. Sequences required for retroviral replication are located in the LTR and are suitable for insertion of the TRE for the transactivation signal of interest. In retrovirus-infected cells, viral transcription occurs from the integrated viral DNAs, the provirus, which represents a transcriptional unit that contains its own regulatory sequences. Expression of the provirus depends on (1) the site into which the provirus has integrated; (2) the physiological state of the cell; and (3) the viral LTR. The expression of the provirus depends almost entirely on host-encoded enzymes.

The viral LTR is derived from three segments of the viral RNA: the R, U5 and U3 sequences. The R or redundant sequence is a short segment (30 to 60 nucleotides) that is present twice in the viral RNA, at the extreme left (5') and right (3') termini. The U5 sequences are present at the 5' end of the viral RNA. The U3 sequences are located upstream from the R sequences and have the most variation in size (0.2 to 1.2 kb) and sequence homology.

Viral specific regulation of expression depends principally on the long terminal repeat (LTR) which contains signals for enhancement, promotion, initiation and polyadenylation of RNA synthesis. Transcription is initiated at the left end of the R sequences in the left-hand LTR. Viral transcription is catalyzed by a cellular type II RNA polymerase and is polyadenylated post-transcriptionally near the right hand end of the right LTR. The U3 regions of all LTRs possess CCAAT and TATAA boxes. Enhancer function has been localized to a repeat sequence of variable length (72 to 101 nucleotides) that is found in U3, upstream from the promoter domain. Sequences in U3 of the MMTV LTR have also been found to be responsible for the enhanced level of virus expression in response to glucocorticoid treatment of MMTV-infected cells.

The U3 region of the LTR has been shown to play an important role in regulating viral expression, as well as regulating tumor formation and disease induction. Therefore the U3 region can be a regulatory region, which if replaced by the TRE of interest would render the recombinant virus responsive to the transactivator expressed by the diseased host cell.

All retroviruses have a similar complement of capsid and envelope proteins. Capsid proteins include the NC and CP proteins, and envelope proteins include the TM and SU proteins. The genes encoding these proteins can serve as regions where foreign DNA sequences can be inserted for the purpose of constructing non-cytocidal-antagonist and cytocidal-antagonist chimeric viruses. Those capsid and/or envelope proteins which have been replaced or disrupted would be supplied in trans, either by vector and/or expressed by host cells, in order to produce virus stocks of the resulting cytocidal-antagonist and non-cytocidal-antagonist chimeric viruses.

Where targeting to the lung is desired, adenoviruses, which display a natural tropism for the lung, may be modified to contain desired TREs that regulate chimeric virus replication. For example, the TRE for the myc oncogene may be advantageously engineered into such viruses in order to treat lung cancers that express the myc oncogene. However, the use of such chimeric adenovirus is not restricted to the treatment of lung disease, since the virus can be inoculated into the desired site to be treated, e.g., breast for the treatment of breast cancer, lung for the treatment of lung cancer, liver for the treatment of hepatocellular carcinoma, etc. Gene sequences required for regulating adenoviral gene expression which can be manipulated in accordance with the invention include region E1, region E3, or between the right ITR and region E4. These regions may be replaced with the TRE of interest and incorporated into viral particles by packaging of the recombinant adenoviral genome.

There are three regions of adenovirus which would be preferred sites for the insertion of foreign DNA sequences for the purpose of engineering non-cytocidal-antagonist and cytocidal-antagonist chimeric viruses. These regions include (a) the EIA region and the major late promoter (MLP); (2) the MLP, together with the tripartite leader; and (3) the replacement of the E3 region. The E3 region has been shown to be dispensable for viral packaging in tissue culture. Chimeric viruses resulting from insertion of foreign DNA sequences in the EIA and MLP regions may be rescued by growth in 293 cells or be co-transfection with a helper virus providing the missing function in trans.

Where targeting to the nervous system is desired, herpes simplex virus which displays a natural tropism for the nervous system, may be modified to contain desired TREs that regulate chimeric virus replication. For example, the TRE for the HIV-tat transactivator may be advantageously engineered into an early promoter region of HSV such as the ICP4 gene sequences or the VP16 gene sequences in order to inhibit HIV expression and infection in microglial cells of the brain.

Several structural genes of HSV can be targeted for the insertion of foreign DNA sequences for the purpose of engineering cytocidal-antagonist and non-cytocidal-antagonist chimeric viruses. For example, the nucleotide sequences encoding the structural glycoproteins, gB, gD and gH can serve as regions to insert foreign DNA sequences. However, those gene products which have been replaced and/or disrupted would be supplied in trans, either by vector and/or expressed by host cells in order to produce virus stocks of the resulting cytocidal-antagonist and non-cytocidal-antagonist chimeric viruses.

The construction and rescue of cytocidal, cytocidal-antagonist and non-cytocidal-antagonist chimeric viruses is described in more detail in the subsections below using MVM as a model virus. However, the principles can be analogously applied to other virus families or strains.

5.1.1. CONSTRUCTION OF CYTOCIDAL CHIMERIC VIRUSES

In one embodiment of the invention, cytocidal chimeric viruses can be designed so that replication of the cytocidal chimeric viruses in response to the transactivating factor produced by the diseased host cell will result in cell death, and therefore will limit the expansion of the diseased cells and/or the further transmission of the pathological infectious agent. The chimeric virus will not replicate in normal or non-diseased host cells; therefore, normal cells infected by the chimeric virus will be spared.

In order to demonstrate the construction of a cytocidal vector, MVMπ was used as the basic tool for the development of the tat-dependent T-cell tropic vectors (described in Section 6, infra). In this recombinant strain, most of the capsid gene of lymphotropic MVMi has been transferred into the prototype MVMp background in the plasmid pMVMπ, which serves as the parental virus, the basic tool of this invention. To generate virus, the plasmid must be transfected into susceptible target cells. For example, the pMVMπ plasmid is transfected into target cells such as the 324K cell line, described in Section 5.2., in order for replication of the viral genome to occur, and progeny virus to be produced. The tropism of the resulting MVMπ virions is directed to T lymphocytes of either murine or human origin. MVMπ infection of human T cells is abortive, leading to high level production of the major non-structural protein NS1, of viral gene products and RF DNA, but little if any, progeny virus.

In a specific embodiment of the invention, pMVMπ was then further modified to generate a chimeric construct, pMVMπTar. pMVMπTar plasmid contains the region of HIV-1 extending from the upstream Spl binding site through the entire stem structure of the TAR element. This insert replaces the Sp1 binding site present in the MVM promoter, its TATAA box and much of the 5' untranslated region of the MVM P4 transcripts (FIGS. 2A–2D). It has been established that the HIV Sp1 sites, in conjunction with the TATAA box are important in establishing tat responsiveness (Olsen et al., 1992, 66:5594–7; Berkhout et al., 1992, J. Virol., 66:139–49). This recombinant construct does not contain the two HIV-1 NF-KB binding sites, therefore it is not NF-κB responsive and does not become activated solely upon T-cell activation.

In the initial construction of pMVMπTar, a unique KpnI restriction site had been engineered at the downstream junction of the HIV and MVM sequences. This effectively sandwiches the region of interest between two restriction sites, unique within the infectious clone, creating a cassette into which chimeric promoters may be inserted by recombinant DNA techniques well known to those skilled in the art.

Different elements of the MVM P4 promoter and the HIV-1 promoter may also be incorporated in order to reduce the basal level of expression from the promoter in the absence of tat, while maintaining a significant elevation of expression at physiologically relevant tat concentrations. For example, Tar-A, Tar-B and Tar-C, as illustrated in FIG. 3, may be constructed which differ by sequential removal of HIV-1 Spl binding sites, with the remaining, most promoter-proximal HIV-1 Spl site being replaced, in Tar-C, by the equivalently-located, but unique Spl site of MVM (Pitluk et al., 1991, J. Virol., 65:6661–70).

By reducing the number of Spl sites, the basal level of transcription from the chimeric promoter may be reduced, without significantly reducing its tat-induced level of expression. The reduction of the amount of sequence in this region derived from HIV-1 may have the added benefit of increasing the packaging efficiency of the constructs by further reducing the overall length of the viral genome.

Other targets in the HIV sequences within the chimeric promoter may be mutated to modulate basal and tat-induced transcription levels. These include sequences involved in the start-site region (SSR) or bipartite activator (Zenzie et al., 1993, J. Biol. Chem., 268:15823–32), and in the novel inducer of short transcript (IST) element (Sheldon et al., 1993, Mol. Cell. Biol., 13:1251–63).

In order to reduce basal level of transcription, the transcription factor binding sites may be mutated within the MVM origin of DNA replication which are located upstream of the HIV insert. Mutating the ATF site away from a transcriptionally active form of this element impairs origin of replication function (Cotmore et al., 1994, EMBO J., 13:4145–4152). Therefore, it is unlikely that a deleterious mutation in this element would result in viable virus. However, the NF-Y binding site is superimposed on the binding site for the viral replicator protein NS1. Furthermore, it appears that the sequence here is a compromise between that required for binding NF-Y and that required for binding NS1, at least at high affinity. Therefore, the introduction of mutations, using recombinant DNA techniques well known to those skilled in the art, should shift the affinity of this site in favor of NS1-binding to retain DNA replication function while reducing basal transcription.

Additional chimeric viruses can be constructed in which elements of the early promoter region of MVM are replaced with TRE sequences derived from regulatory regions of the Human T-cell lymphotropic virus (HTLV). HTLV infection is linked to a number of clinical diseases, most notably adult T-cell leukemia/lymphoma and the syndrome known as HTLV-associated myelopathy. The HTLV-1 trans-activator protein, Tax, activates the transcription of a viral promoter through multiple enhancer elements, ultimately leading to cell transformation, immortalization and disease (Yoshida, 1993, Trends Microbiol. 1:131–135).

MVM plasmids can be modified to generate a chimeric construct, pMVM-Tax. The pMVM-Tax plasmid would contain one or more, of the three 21 base pair repeats known to be responsive to Tax, found in the U3 region of the HTLV genome (Yoshida, 1993, Trends Microbiol. 1:131–135). This insert replaces the analogous sequences present in the MVM P4 promoter region (FIGS. 2A–2D). It has been established that the Tax protein interacts with cellular enhancer proteins, including CREB, NF-kappa B and SRF.

In other embodiments, elements of the early promoter region of MVM can be replaced with TRE sequences derived from the regulatory regions of the hepatitis B virus (HBV). Such chimeric viruses could be used to treat HBV-infection. The hepatitis B virus HBX protein is a transactivator of transcription which is required for viral infection and has been implicated in virus-mediated liver oncogenesis (Zahm et al., 1988, Oncogene 3:169–177). HBX transactivates both Enhancer I and II of the HBV genome (Spandau and Lee, 1988, J Virol. 62:427–434). The dependence of viral infection upon HBX expression may provide its use as an antagonist to interfere with and suppress HBV infection.

MVM plasmids can be modified to generate the chimeric constructs, pMVM-HBEnI and pMVM-HBEnII. The pMVM-HBEnI plasmid would contain the HBX responsive region, Enhancer region I, which extends from nucleotide 950 to 1150 of the 3.2-kb HBV genome (Spandau and Lee, 1988, J Virol. 62:427–434). The pMVM-HBEnII plasmid contains the HBX responsive region, Enhancer region II, which extends from nucleotide 1646 to 1715. These inserts replace the analogous sequences present in the MVM P4 promoter region (FIG. 2).

In other embodiments, elements of the early promoter region of MVM may be replaced with TRE sequences derived from the regulatory regions of the herpes simplex virus (HSV). Such chimeric viruses can be used to treat herpes virus infection. The HSV gene product ICP4 is a transactivator of transcription of HSV early and late genes and is essential for a full lytic HSV life cycle.

MVM plasmids can be further modified to generate the chimeric construct pMVM-ICP4. The pMVM-ICP4 plasmid contains the ICP4 responsive element which consists of the nucleotide sequence 5' ATCGTCCACACGGAG 3' which is found across the transcription initiation site of the a4 gene of HSV. This insert replaces the analogous sequences present in the MVM P4 promoter region.

In another embodiment, elements of the early promoter region of MVM can be replaced with nucleotide sequences corresponding to the Myc responsive element. Such chimeric viruses can be used to treat cancers in which the Myc transcription factor is overexpressed, including but not limited to Burkitt's lymphoma, small cell lung carcinomas, and glial blastomas. The over-expression of the Myc transcription factor results in uncontrolled cellular proliferation (Prendergast and Ziff, 1992, Trends in Genetics 8:91–96).

MVM plasmids can be modified to generate the chimeric construct pMVM-Myc. The pMVM-Myc construct contains the MYC responsive element which consists of the nucleotide sequence 5' CACGTG 3' (Kretzner et al., 1992, Nature 359: 426–429). This insert replaces the analogous sequences present in the MVM P4 promoter region.

In other embodiments, elements of the early promoter region of MVM can be replaced with nucleotide sequences corresponding to HOX11 responsive element to generate chimeric viruses for the treatment of leukemias. T-cell acute leukemias have a number of different recurring translocations. Most of these involve putative transcription factors, are involved in differentiation and are not normally expressed in T cells. An example is the HOX11 gene which encodes a homeodomain protein that can bind DNA and activate target genes in T cells contributing to T-cell acute leukemias (Dear at al., 1993, Proc. Natl. Acad. Sci. USA 90:4431–4435.).

MVM plasmids can be modified to generate the chimeric construct pMVM-HOX11. The pMVM-HOX11 construct would contain a HOX11 responsive element which consists of the nucleotide sequence 5' TAATGGTAATGGTAATGG-TAATGGTATGGTAATGG 3'. The insert would replace the analogous sequences present in the MVM P4 promoter region.

In further embodiments of the invention, MVM plasmids are modified to generate chimeric constructs containing those heterologous sequences which respond to other target viral and/or pathogenic transactivators. These inserts replace the analogous sequences found in the MVM P4 promoter region.

5.1.2. CONSTRUCTION OF CYTOCIDAL-ANTAGONIST CHIMERIC VIRUSES

The cytocidal chimeric virus can be further engineered so that a region of the viral genome that is non-essential or complementable for viral replication is modified to contain an additional sequence encoding a product that inhibits the expression or activity of a different gene product involved in the disease pathway, or one which inhibits replication of the infectious pathogen. Such cytocidal-antagonist chimeric viruses will both inhibit replication and spread of the pathogen, and kill infected and diseased host cells.

In this embodiment of the invention, nucleotide sequences derived from coding and non-coding regions and/or regulatory regions of the target virus or pathogenic agent may be used to prevent its own expression. Given that the nucleotide sequences of the target viruses and pathogenic agents, such as HIV, HBV, HTLV, HSV, and the mutations and translocations of most cancers are known, several techniques may be employed to down-regulate target viral and/or pathogenic gene expression, including but not limited to, use of dominant negative mutants, antisense, triple helix, and ribozyme approaches. Administration of these nucleotide sequences therefore may temporarily block expression and/or transcription of target pathogenic genes.

For example, the parvoviral gene encoding the capsid protein, which is complementable for parvoviral replication can be replaced with a sequence that encodes a product which inhibits HIV replication. Stocks of the resulting chimeric virus can be produced using host cells and/or vectors that supply the transactivating factor required for replication, and the parvoviral coat protein in trans. The resulting virus both inhibits HIV replication and kills the infected cell, due to the expression of parvoviral NS gene products.

In a specific embodiment of the invention, the cytocidal vector pMVMπTar, as described in Section 5.11., is modified to contain nucleotide sequences in the capsid gene of MVM to inhibit HIV-replication. In order to facilitate these constructions within the capsid gene in MVM, an intermediate clone containing predominantly coat protein sequences may be utilized. The intermediate cloning vehicle for capsid region substitutions may be constructed by cloning a fragment of LuIII using recombinant DNA techniques well known to those skilled in the art. LuIII is a parvovirus closely related in sequence to MVM, more so at the protein level than at the nucleotide level (Diffoot et al., 1993, Virology, 192:339–45). This sequence contains fairly uniformly dispersed nucleotide mismatches to the corresponding MVM sequence which should suppress homologous recombination with the MVM capsid gene sequences providing helper functions in trans. The PCR-generated fragment may be produced from a primer upstream of the HindIII site at nucleotide (nt) 2648 to a SacI site incorporated into the most rightward primer, located just beyond the C-terminus of VP2, at nt 4558. The resulting ~2kb fragment may then be cut with HindIII and SacI and cloned between these sites in the polylinker of pUC19, to produce the cloning intermediate pLu-cap. This insert contains several restriction sites situated downstream of the normal VP2 start site at distances convenient for the substitution of various sizes of foreign DNA. The modified LuIII coat protein gene segment in pLu-cap, shown in FIG. 4 is the recipient for each target virus antagonist sequences, which are inserted so as to replace all or part of the VP2 gene by using either naturally occurring restriction sites or sites engineered on to their ends using oligonucleotide primers coupled with PCR technology.

Any nucleotide sequence that encodes a gene product or transcript that works to inhibit HIV-replication can be engineered into the expression cassette of the parvoviral vectors to yield the cytocidal-antagonist chimeric virus, i.e. one that inhibits-HIV replication and kills the infected host cell. HIV-antagonist sequences include, but are not limited to: (1) hair-pin ribozymes directed at a CGUC motif within the leader sequence of HIV mRNA (Ojwang et al.,1992, Proc. Natl. Acad. Sci. 89: 10802–6); (2) antisense sequences; (3) triple helix structures; (4) decoy RNAS; (5) dominant-negative mutants; or (6) sequences encoding the Fab domain of an antibody that neutralizes the activity of the HIV gene product. The cloning of HIV-antagonist cassettes can follow the general principles outlined above or any other methods well known to those skilled in the art. Such cassettes alone, or multiple copies of them, may be placed between restriction sites convenient for their exact, or close to exact, substitution for LuIII sequences within pLu-cap. The expression cassette in pLu-cap is large enough to accommodate several potential antagonist sequences with established HIV-antagonist activity.

The invention encompasses "classical" antisense strategies, testing regions identified by others as having efficacy in long-term transduced cell situations. Anti-sense RNA and DNA molecules act to directly block the translation of mRNA by binding to targeted mRNA and preventing protein translation, either by inhibition of ribosome binding and/or translocation or by bringing about the nuclease degradation of the mRNA molecule itself.

Antisense sequences to be used to include, but are not limited to those identified in the gag region and the HIV polyA site (Chatterjee et al., 1992, Science, 258:1485–8; Sczakiel et al., 1992, J. Virol., 66:5576–81; Rittner et al., 1991, Nucleic Acids Res., 19:1421–6), provided that the antisense does not interfere with vector replication in producer cells.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of target viral genes.

Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

The present invention also includes individual antisense sequences separated by self-cleaving ribozyme sequences, and other such adaptations designed to increase their effectiveness.

In an alternative embodiment, oligonucleotides designed to hybridize to the 5' region of the target gene (including the region upstream of the coding sequence) and form triple helix structures may be used to block or reduce transcription of the target gene. In yet another alternative, these vectors may be utilized for gene replacement, in which nucleic acids encoding the full length wild-type target message may be introduced in vivo into cells which otherwise would be unable to produce the wild-type target gene product in sufficient quantities or at all.

In another embodiment of the invention RNA decoys are used as a further strategy of antagonist expression. RNA decoys are short RNA oligonucleotides corresponding to the HIV rev response element (RRE). The RNA decoy strategy is based on the expression of short RNA transcripts corresponding to the RRE which will compete for the binding of Rev to its physiological targets on the viral RNA. The minimal RNA oligonucleotide shown to encode the Rev-binding domain consists of: 5' UGGGCGCUUCGGCG-GUACA 3' (Lee et al., 1994, J. Virol. 68: 8254–8264).

In a preferred embodiment, the antisense, ribozyme, triple helix nucleotides and decoy RNAs are designed to inhibit the translation or transcription of the target with minimal effects on the replication of the chimeric virus. To accomplish this, the oligonucleotides used should be designed on the basis of relevant sequences unique to the target; i.e., those sequences found in the target and not in the chimeric viral genome.

In another embodiment of the invention, dominant-negative mutant forms of the HIV env or rev gene products can be engineered into the expression cassette of the chimeric parvoviral vector. The expression of such defective mutant HIV proteins in the host cell will inhibit the propagation of HIV. The rev protein interacts with an RNA sequence termed the rev responsive element (RRE) located within the env gene, and this interaction is essential for the cytoplasmic expression of the unspliced, "late" HIV RNAs, which encode the structural proteins. The functionally defective rev mutant M10, in which the leucine and glutamic acid residues at positions 78 and 79 are changed to aspartic acid and leucine, respectively, exhibits a strong dominant negative phenotype when expressed in transient assays and constitutively in retrovirally transduced cells (Bevec et al., 1992, Proc. Natl. Acad. Sci. USA 89:9870–9874; Malim et al., 1992, J. Exp. Med. 176:1197–1201; Bahner et al., 1993, J.Virol. 67:3199–3207; Liem et al., 1993, Human Gene Therapy 4: 625–634). The mutant rev can be prepared from the wild type clone by site-directed mutagenesis (Sambrook et al., 1989, Molecular Cloning, A Laboratory Manual, 2nd Ed., Cold Spring Harbor Press, N.Y.), and substituted into pLu-cap as described above.

Alternatively, a soluble form of the CD4 glycoprotein, the major cell surface receptor for HIV, or a CD4 fusion protein that is retained by the endoplasmic reticulum (ER) and Golgi apparatus can be engineered into the chimeric parvovirus. The retention of CD4 in the ER will result in CD4 complexing with HIV gp120/41 in the ER and prevent its transport to the cell surface (Buonocore and Rose, 1990, Nature 345: 625–628; Buonocore and Rose, 1993, Proc. Natl. Acad. Sci. USA 90:2695–2699). The coding sequence for the mutant CD4 protein can be obtained from the original plasmid pBS-CD4-KDEL (Buonocore and Rose, 1990, Nature 345: 625–628), using PCR or other recombinant DNA techniques well known to those skilled in the art, and designed to incorporate the appropriate cloning sites at either end for insertion into the translation start site for the VP2 in pLu-cap. Alternatively, an inhibitor of the HIV-1 protease can be engineered into the chimeric parvovirus. The HIV-1 protease is required for HIV replication (Ho et al., 1995, Nature 373: 123–126), therefore inhibition of this protease should inhibit propagation of HIV.

Additional cytocidal-antagonist viruses can be constructed in which nucleotide sequences that encode a gene product or transcript that inhibits HTLV-I and-II replication can be engineered into a non-essential or complementable region of the chimeric parvoviral genome. For example, the gag, pol, and env genes of HTLV code for the structural proteins, reverse transcriptase, and envelope protein of the virus can be targeted to disrupt HTLV replication using the methods including, but not limited to: antisense RNAS, triple helix, ribozyme approaches, and dominant negative mutants as outlined above.

Additional cytocidal-antagonist viruses may be constructed in which nucleotide sequences that encode a gene product or transcript that inhibits HBV replication can be engineered into a non-essential or complementable region of the chimeric parvoviral genome. For example, the HBV surface antigen, core antigen and viral DNA polymerase of HBV can be targeted to disrupt HBV replication using the methods including, but not limited to: antisense RNAs, triple helix, ribozyme approaches, and dominant negative mutants as outlined above.

In yet another embodiment of the invention, cytocidal-antagonist viruses can be constructed in which nucleotide sequences that encode a gene product or transcript that inhibits HSV replication. For example, several structural glycoproteins of HSV may be targeted, including, but not limited to gB, gD and gH, which have been shown to be essential for HSV infection of cells and generation of infectious viral progeny (Roizman et al., 1981, Herpesviridae. Intervirology 16:201), can be targeted to disrupt HSV replication using the methods including, but not limited to: antisense RNAs, triple helix, ribozyme approaches, and dominant negative mutants as outlined above.

5.1.3. CONSTRUCTION OF NON-CYTOCIDAL-ANTAGONIST CHIMERIC VIRUSES

In another embodiment of the invention, the chimeric cytocidal virus can be designed so that it is non-cytocidal-antagonist by incorporation of a negative feedback loop that limits both the production of the pathogen and expression from the chimeric virus. In particular, the cytocidal chimeric virus can be further engineered so that a region of the viral genome which is non-essential or complementable for viral replication is modified to contain a nucleotide sequence encoding a product that inhibits the production or activity of the transactivation signal produced by the diseased host cell. Decreased expression of the transactivator will inhibit replication of both the pathogenic infectious agent and the chimeric virus, through a negative feedback loop, thus allowing the host cell to live as long as the pathogen is suppressed.

As an example of this embodiment of the invention, any nucleotide sequence that encodes a gene product or transcript that inhibits HIV tat production or activity can be engineered into a complementable capsid region of the chimeric parvoviral genome to yield a non-cytocidal-antagonist virus. Stocks of the resulting chimeric virus can be produced using host cells and/or vectors that supply, in trans, the parvoviral coat protein and HIV-tat in a manner that is not inhibited by the antagonist gene product. The non-cytocidal-antagonist chimeric virus operates through the negative feedback loop so that replication of both HIV and the chimeric parvovirus are shut down, and the host cell survives. Several techniques can be employed to down-regulate the transactivation signal produced by the diseased host cell, including but not limited to antisense, triple helix and ribozyme approaches.

In order to facilitate these constructions within the capsid gene in MVM, an intermediate clone containing predominantly coat protein sequences may be utilized. The intermediate cloning vehicle for capsid region substitutions may be constructed by cloning a fragment of LuIII using recombinant DNA techniques well known to those skilled in the art. LuIII is a parvovirus closely related in sequence to MVM, more so at the protein level than at the nucleotide level (Diffoot et al., 1993, Virology, 192:339–45). This sequence contains fairly uniformly dispersed nucleotide mismatches to the corresponding MVM sequence which should suppress homologous recombination with MVM capsid gene sequences providing helper functions in trans. The PCR-generated fragment may be produced from a primer upstream of the HindIII site at nucleotide (nt) 2648 to a SacI site incorporated into the most rightward primer, located just beyond the C-terminus of VP2, at nt 4558. The resulting ~2 kb fragment may then be cut with HindIII and SacI and cloned between these sites in the polylinker of pUC19, to produce the cloning intermediate pLu-cap. This insert contains several restriction sites situated downstream of the normal VP2 start site at distances convenient for the substitution of various sizes of foreign DNA. The modified LuIII coat protein gene segment in pLu-cap, shown in FIG. 4 is the recipient for each target virus antagonist sequences, which are inserted so as to replace all or part of the VP2 gene by using either naturally occurring restriction sites or sites engineered on to their ends using oligonucleotide primers coupled with PCR technology.

Any nucleotide sequence that encodes a gene product or transcript that works to inhibit HIV-tat expression or activity can be engineered into the expression cassette of the parvoviral vectors to yield the non-cytocidal-antagonist chimeric virus, i.e. one that inhibits both HIV-tat expression and replication of the chimeric virus. HIV-antagonist sequences include, but are not limited to: (1) hair-pin ribozymes directed at a CGUC motif within the leader sequence of all HIV-tat (Ojwang et al.,1992, Proc. Natl. Acad. Sci. 89: 10802–6); (2) antisense sequences that inhibit translation of tat mRNA; or (3) triple helix structures that inhibit transcription of tat mRNA. The cloning of HIV-antagonist cassettes can follow the general principles outlined above or any other methods well known to those skilled in the art. Such cassettes alone, or multiple copies of them, may be placed between restriction sites convenient for their exact, or close to exact, substitution for LuIII sequences within pLu-cap.

The invention encompasses nucleotide sequences encoding an antisense sequence with established HIV-tat antagonist activity; that is a nucleotide sequence encoding an antisense molecule that complements and blocks translation of HIV-tat mRNA (Chatterjee et al., 1992, Science 258:1485–8; Sczakiel et al., 1992, J. Virol. 66:5576–81; Rittner et al., 1991, Nucleic Acids Res. 19:1421–1426).

The invention also encompasses a nucleotide sequence encoding a ribozyme that cleaves the HIV-tat mRNA and prevents its translation, to be inserted in place of the complementable capsid gene of parvovirus. Within the scope of the invention are engineered hammerhead motif ribozyme molecules that specifically and efficiently catalyze endonucleolytic cleavage of HIV-tat or other transactivating factor transcripts. Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the HIV-tat coding sequence containing the cleavage site may be evaluated for predicted structural features such as secondary structure that may render the oligonucleotide sequence unsuitable.

The expression cassette in pLu-cap is large enough to accommodate several potential HIV-tat antagonist sequences. Therefore, several HIV-tat antisense sequences, and/or several HIV-tat ribozymes may be included in the expression cassette. The present invention also includes individual antisense sequences separated by self-cleaving ribozyme sequences, and other adaptations designed to increase their effectiveness.

In an alternative embodiment, a transcript that forms a triple helix with the HIV-tat regulatory region and thus prevents transcription of tat can also be utilized. Oligonucleotides or short transcripts designed to hybridize to the 5' region of the target gene (including the region upstream of the coding sequence) and form triple helix structures can be used to block or reduce transcription of the target gene.

In another embodiment of the invention RNA decoys are used as a further strategy of antagonist tat expression. RNA decoys are short RNA oligonucleotides corresponding to the HIV transactivation response element (TAR). The RNA decoy strategy is based on the expression of short RNA transcripts corresponding to the TAR which will compete for the binding of Tat to its physiological targets on the viral RNA.

In another embodiment of the invention, non-cytocidal-antagonist vectors can be designed to inhibit HTLV-I and -II replication while allowing the host cell to survive. The pMVM-Tax virus can be engineered to encode antagonist Tax sequences, including but not limited to tax antisense, ribozymes that cleave tax mRNA, and short transcripts designed to form triple helix structures with the tax regulatory region, thereby preventing transcription of tax.

In another embodiment of the invention, non-cytocidal-antagonist vectors can be designed to inhibit HBV replication while allowing the host cell to survive. The pMVM-HBEnI and pMVM-HBEnII virus can be engineered to encode antagonist HBX sequences, including but not limited to HBX antisense, ribozymes that cleave HBX mRNA, and short transcripts designed to form triple helix structures with the HBX regulatory region, thereby preventing transcription of HBX.

In another embodiment of the invention, non-cytocidal-antagonist vectors can be designed to inhibit HSV replication while allowing the host cell to survive. The pMVM-ICP4 virus can be engineered to encode antagonist ICP4 sequences, including but not limited to ICP4 antisense, ribozymes that cleave ICP4 mRNA, and short transcripts designed to form triple helix structures with the ICP4 regulatory region, thereby preventing transcription of ICP4.

5.2. PRODUCTION OF RECOMBINANT VIRUS STOCKS

Another aspect of the invention relates to methods for replicating and packaging the chimeric viruses. Chimeric viral stocks may be produced by transfecting an appropriate cell type with the chimeric viral vector. The host cell/vector system must express and supply the necessary transactivator and other viral functions required for chimeric viral replication in trans. The present invention also encompasses host cell lines expressing high levels of transactivating protein for large scale production of chimeric viruses. An additional aspect of the invention relates to methods for replicating and packaging the cytocidal-antagonist and non-cytocidal-antagonist chimeric viruses. Recombinant viral stocks of these viruses may be obtained using host cells and/or vectors that provide both the essential transactivator and the capsid protein. In these chimeric viruses, complementable capsid regions have been replaced with nucleotide sequences antagonistic to the target viral and/or pathogenic agent. Therefore, it is essential to provide the capsid or coat proteins in trans in order to have efficient packaging of the cytocidal-antagonist and non-cytocidal-antagonist chimeric viruses. The capsid or coat proteins may be supplied by host cells or vectors which express the required structural protein.

The transactivator may be provided in trans by autonomously replicating plasmids that lack functional chimeric viral replication and packaging elements. Such DNA may be propagated in microorganisms, for example, such as bacteria, yeast, insect cells or animal cells as part of a plasmid, cosmid, YAC bacteriophage or appropriate viral-based vectors. To this end, the entire wildtype viral genome lacking functional replication and packaging elements, portions of the wildtype viral genome, or cDNA coding for the required transactivator may be incorporated into recombinant helper plasmids, bacteriophages, cosmids, YAC, etc. by methods well known in the art.

Various additions and modifications may be made to these particular vectors to increase the levels of expression of the transactivator. For example, DNA sequences that permit autonomous replication in mammalian cells may be inserted into the recombinant helper plasmids. Autonomous replication of these plasmids will increase the number of templates available for transcription of the helper DNA resulting in an increased production of viral replication and packaging proteins. Autonomous replication sequences that may be utilized include, but are not limited to, those sequences found in viruses such as SV40, papilloma, CMV or EBV. Alternative eukaryotic expression systems which may be used to express the helper functions are yeast transformed with recombinant yeast expression vectors; insect cell systems infected with recombinant virus expression vectors (e.g., baculovirus); or plant cell systems infected with recombinant virus expression vectors (e.g., cauliflower mosaic virus, CaMV; tobacco mosaic virus, TMV) or transformed with recombinant plasmid expression vectors (e.g., Ti plasmid).

In another embodiment, cell lines may be engineered to stably express the transactivator. Stable expression can be accomplished using selectable and/or amplifiable markers to ensure integration of the DNA into the host cell chromosome. For example, following the introduction of DNA encoding the transactivator, engineered cells may be allowed to grow for 1–2 days in an enriched media, and then are switched to a selective media. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072; neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Transfection may be performed by the DEAE-dextran method (McCutchen and Pagano, 1968, J. Natl. Cancer Inst. 41:351–357), the calcium phosphate procedure (Graham et al., 1973, J. Virol. 33:739–748) or by any other method known in the art, including but not limited to microinjection, lipofectin, and electroporation. Amounts of recombinant vector and helper DNA used in transfections are often from 0.2 $\mu$g to 10 $\mu$g of DNA per $10^6$ cells, but vary among different DNA constructs and cell types. These ranges are not rigid. Cell lines suitable for transfection of recombinant vectors include any cell line permissive for parvoviral, retroviral and adenoviral infection.

In a specific embodiment of the invention wherein chimeric viruses are designed to treat HIV-infection, the chimeric viral genome is expressed in tat-expressing producer lines, such as 324K-derived cell lines. An example of such a cell line is derived by co-transforming 324K cells, an SV40-transformed human fibroblast cell line capable of sustaining productive MVMP and MVMi growth (Tattersall and Bratton, 1983, J. Virol. 46:944–55), with both a tat expression plasmid, either pSV2-tat or pCG-tat, in which tat is driven off the human cytomegalovirus immediate early promoter, and a dominant selectable marker, in this case pSV2-neo.

The invention also includes cell lines which depend on constitutive tat expression for survival in selective medium, such as 324 tat-A3. In the production of this cell line the dominant selectable marker gene, neo, was inserted in place of the *E. coli* β-galactosidase (β-gal) gene fragment, in the HIV-1 LTR-driven reporter vector pHIV-LacZ, to produce a construct, pHIV-neo. This construct is co-transfected with pSV2-tat or pCG-tat into 324K cells, followed by selection in medium containing different levels of G418.

A more preferable embodiment of the invention are host cell lines expressing high levels of transactivating protein in response to infection with MVM and its derivatives. Such cell lines may be developed by introducing the gene sequences encoding the transactivating protein into the cellular chromosome under control of MVM P38 late promoter. This promoter, which is normally silent, is strongly transactivated by the MVM NS1 gene product, therefore the low level of NS1 produced by the basal level of transcription of even the most tat-dependent chimeric P4 promoter constructed, would be enough to induce some tat expression.

In order to facilitate construction of cell lines expressing genes to be driven by the MVM P38 promoter, an expression cassette clone has been constructed, in which P38 is placed upstream of several six-base restriction sites, for gene insertion, followed by a rabbit β-globin intron and polyadenylation signal. The P38 promoter itself is situated downstream of duplicated SV40 poly-adenylation sites, in order to minimize transcription through the cassette from upstream promoters when it is integrated in the host cell chromosome. The HIV-1 tat cDNA from pSV2-tat72 has been cloned into this construct to produce pP38-tat, in preparation for making new production cell lines. Cell lines may be co-transfected with pP38-tat:pSV2-neo at a 10:1 DNA ratio, and selected in G418.

Producer cell lines of the present invention also include murine T-cell lines, such as S491TB2, which is the preferred laboratory host for MVMi-like viruses. Such cell lines may be transfected with a tat expression construct. Other suitable cell lines include Chinese hamster ovary cells and their human hybrids, as well as murine fibroblast:T-cell hybrids expressing the required transactivator described in Section 5.1., supra.

Tat-dependent virus stocks can be used to screen G418-resistant clones by fluorescent antibody staining for their ability to support NS1 synthesis after infection with MVMπTar-2. Positive cell lines are then grown up and compared by Southern blot analysis of virus yield for their efficiency in supporting MVMπTar-2 growth, and for their ability to support plaque formation by the MVMπTar viruses.

5.3. IN VITRO TESTING OF CHIMERIC VIRUSES

In order to determine the activity of each of the chimeric viruses generated using the methods described herein, a number of parameters of virus growth and cellular response in different cell populations under different conditions may be assayed. The level of viral protein expression and DNA replication may be determined, including any concomitant cell killing in a series of relevant cells, such as H9 and Jurkat cells. In the case of HIV and HTLV, relevant cells also include primary human peripheral blood lymphocytes, both for the original virus and for various constructions. These analyses may precede those exploring the ability of these chimeric viruses to interfere with HIV replication, since it is important for the viruses to be non-toxic to normal proliferating primary lymphocytes in order to be therapeutically useful.

As an illustration of the testing procedure, MVMπ parental virus and MVMπTar viruses are initially compared for their ability to infect and kill PHA-stimulated human peripheral blood leukocytes. The human cells may be purified from blood collected from normal donors by Ficoll-hypaque density gradient centrifugation. Primary human peripheral mononuclear cells are susceptible to infection by the murine lymphotropic parvovirus MVMi and its derivatives, and this infectious cycle is suppressed in the recombinant virus containing the MVM/HIV chimeric promoter.

Experimental infections of primary cells may be carried out using gradient purified virions. Initially such infections are set up in several different ways in order to investigate both the requirements for parental (i.e. non-tat-dependent) viral replication and gene expression in these cells, and the effects of virus infection on cellular physiology. For instance, it is important to establish the multiplicity dependence of viral replication and cell growth inhibition for the parental and chimeric viruses, and whether there is a difference in the interaction if the cells are stimulated prior to infection with MVM or after the virus has been added.

In vitro assays also include the appearance of viral NS proteins and replicative DNA. The appearance of viral macromolecules in such cells may be monitored by Southern and Western blotting and immunofluorescence, as described below.

In order to establish the effect of parental and chimeric viruses on the responsiveness of these quiescent primary cells to mitogenic stimulus, parallel cell cultures may be infected with the same range of multiplicities of the viruses followed by the $^{3}$H-thymidine labelling. Careful kinetic studies, using low percent agarose gel electrophoresis (Cotmore et al., 1987, Advances in Virus Research, 33:91–174) can distinguish cellular and viral DNA replication. Control cultures are monitored where the cells have been exposed to purified empty capsids, rather than live virus, in order to distinguish effects of intracellular viral gene expression from the exogenous application of viral particles. In vitro assays of the present invention also include assaying if multivalent binding of virus to cell surface receptors on quiescent cells may mimic an activation signal.

Further comparison of chimeric viruses and their parent may be carried out in continuous T-cell lines such as Jurkat, and their derivatives which constitutively express tat, such as Jurkat-Tat. Multiplicity-dependent killing by chimeric and wildtype MVM may be determined by standard assays for cell survival and killing, i.e. fluorimetric analysis of surviving cells in a multiwell format. Briefly, cells are seeded in the wells of microtitre plates and varying quantities of purified virus added. At different times after infection, non-fluorescent, activatable indicator is added to the cells and incubated for a further 2–4 hours, at which time the plates are read in a fluorimeter. The results are then compared with a standard curve generated with varying concentrations of uninfected cells, and selected duplicate wells without indicator are examined by trypan blue staining for confirmation of the result. The results of these assays are used, in conjunction with the molecular analyses described earlier, to evaluate the effects of changes within the chimeric promoter.

In order to determine the activity of the cytocidal-antagonist chimeric viruses, it is also desirable to measure the anti-viral and/or anti-pathogenic activity. For example, the anti-HIV cytocidal-antagonist chimeric viruses should be assayed for their anti-HIV activity in addition to target cell killing activity. Anti-HIV activity can be measured by a number of methods, well known to those skilled in the art. For example, anti-HIV activity of the cytocidal-antagonist vector can be determined by measuring levels of gag and env proteins by immunoassay or by measuring reverse transcriptase activity, as assayed by the method developed by Goff (Goff et al., 1981 J. Virol. 38:239–248). Briefly, in this assay, supernatants from HIV virus/cell cultures, infected or non-infected with the anti-HIV cytocidal-antagonist chimeric virus are adjusted to 1% Triton-X100. A 10 $\mu$l sample of the supernatant is added to 50 $\mu$l of RT cocktail in a 96-well U-bottom microtitre plate and the samples are incubated at 37° C. for 90 min. The RT cocktail contains 75 mM KCL, 2 mM dithiothreitol, 5 mM $MgCl_2$, 5 $\mu$M/ml poly A (Pharmacia, cat. no. 27-7858-01), 0.05% NP40, 50 mM Tris-HCL, pH 7.8, 0.5 $\mu$M non-radioactive dTTP, and 10 $\mu$i/ml $^{32}$P-dTTP (Amersham, cat. No. PB.10167).

After the incubation period, 40 $\mu$l of reaction mixture is applied to a Schleicher and Schuell (S+S) NA45 membrane (or DE81 paper) saturated in 2 X SSC buffer (0.3M NaCl and 0.003M sodium citrate) held in a S+S Minifold over one sheet of GB003 (S+S) filter paper, with partial vacuum applied. Each well of the minifold is washed four times with 200 $\mu$l xSSC, under full vacuum. The membrane is removed from the minifold and washed two more times in a pyrex dish with an excess of 2xSSC. Finally, the membrane is drained on absorbent paper, placed on Whatman #3 paper, covered with Saran wrap, and exposed to film overnight at −70° C.

HIV replication can also be determined by measuring levels of secreted p24, the major core antigen of HIV. Secreted p24 can be measured by a standard ELISA assay. The number of cells infected with HIV can be determined by measuring the intracellular expression of p24 in individual cells by using immunofluorescence staining and flow cytometry. This assay permits the simultaneous determination of the fraction of infected cells in the population and the amount of p24 expressed in individual cells.

5.3.1. SCREENING RECOMBINANT VIRAL REPLICATION AND CYTOTOXICITY IN A PANEL OF DIVERSE CELL TYPES

In accordance with the present invention, recombinant MVM based viruses are also assayed for their ability to infect cells outside of the T cell compartment, and to what extent the modification of the P4 promoter to make NS gene expression tat dependent would hold in such cells. This assay would entail a comparison of chimeric and parental virus replication and cell killing in a panel of normal and tumor-derived human cell types of diverse differentiated phenotypes. While it is not possible to test representatives of each of the myriad of differentiated cell types that make up the human body, this aspect may by explored by assembling a panel of diverse cell types, and examining them for their ability to support MVMπ-2 NS gene expression and DNA replication. The cell lines to be tested may be purchased from the American Type Culture Collection, and will be chosen, where possible, as paired cultures which are known to express at least one differentiation marker, either cytological or biochemical, characteristic of their tissue of origin.

Cells are initially screened for virus binding and production of replicative DNA species at high multiplicity. Multiple cultures of rapidly dividing cells of each cell type are infected at 30–100 pfu per cell with MVMπ-2 for 4 hours at 37° C. under appropriate conditions. After thorough washing, total cellular DNA is prepared from one set of cultures while the rest are returned to their appropriate culture conditions for periods of 24 and 48 hours. After this period of incubation, total cellular DNA is prepared and all samples analyzed by Southern blotting using an MVM probe, including controls of both infected and uninfected 324K cells. A signal at both time points at the position of viral DNA indicates that the cells bear receptors capable of binding virus. Signal at 5 and 10 kb in the later samples indicates that the cells also support viral DNA replication.

Cells which show no signal at any time point are eliminated from further analysis. Cells showing signal only at the position of viral single-stranded DNA are analyzed further by Western blotting using anti-NS1 antibody, to detect viral gene expression in the absence of DNA replication. This has been shown to be the pattern for infection of a pair of normal human fibroblast cultures, HELF and HFF, with MVMp. When the panel has been reduced to those cell lines showing NS protein and/or DNA replication responses to VMπ-2 infection, these cells are then analyzed, with the appropriate assays, for the suppression of this signal in infections with each of the chimeric viruses. These assays may be performed at a range of multiplicities, and run in parallel with cell survival assays.

A profile of target cell specificities may be generated for the MVMi-based viruses in this manner, including whether the introduction of the HIV Tar sequences, with and without their associated upstream elements, would suppress viral gene expression and cytotoxicity in each cell line. The results should provide an indication as to whether the vector system is likely to afford the type of specificity and selectivity sought.

5.3.2. TESTING OF RECOMBINANT CHIMERIC VIRUSES IN ANIMAL MODELS

Once the tat-dependent, replication competent MVM/HIV chimeric viruses are obtained, their safety and efficiency may be tested in animal models. In recent years, severe combined immunodeficient mice have been transplanted with human bone marrow cells, which are used to support HIV infection in mice. Therefore, such SCID/Hu mice may be used to test the in vivo therapeutic effects of the chimeric viruses described herein. In addition, the viruses may also be tested in Rhesus macaques, in the control of infection by the Simian Immunodeficiency Virus $SIV_{mac}$. However, since chimeric viruses containing the HIV-1 LTR may not be activated efficiently by the tat protein encoded by $SIV_{mac}$ (Cullen et al., 1992, AIDS Res. Hum. Retroviruses, 8:387–93; Sakai et al., 1993, Arch Virol., 129:1–10), a series of chimeras may be constructed, analogous to those described above, with transcriptional elements derived from the $SIV_{mac}$ LTR. Since transfection and reconstruction experiments reported in the art have shown that the $SIV_{mac}$ LIR is efficiently transactivated by HIV-1 tat (Cullen et al., 1992, AIDS Res. Hum. Retroviruses, 8:387–93; Sakai et al., 1993, Arch Virol., 129:1–10), it does not seem likely that new host cell lines expressing $SIV_{mac}$ tat will be required. Before embarking on the MVM/SIV chimeric promoter studies, however, the infection experiments with MVMi, MVMπ and MVMp viruses may be repeated with the Herpesvirus saimiri-transformed macaque T-cells in order to ensure that the MVM variants can indeed infect simian T-cells. Since several monkey cell lines can be infected with MVM, and Rhesus macaques have been shown to be susceptible to infection with the closely related H-1 virus (Toolan, H. W., 1966, Nature, 209:833–4), it is likely that Rhesus macaques will be susceptible to infection with MVM-based viruses.

5.4. USES OF CHIMERIC VIRUSES

The chimeric viruses of the present invention are attractive as delivery vehicles for genetic therapy in humans. The parvovirus embodiment described herein is particularly attractive for this purpose because they comprise the only family, among DNA viruses, in which there are no tumorigenic members, indeed they are markedly oncosuppressive under many circumstances (Rommelaere et al., 1991, J. Virol. Methods, 333:233–51; Rommelaere et al., 1990, Handbook of Parvoviruses, p. 41–58; Cotmore et al., 1987, Advances in Viral Research, 33:91–174). This lack of potential for causing cellular transformation should give the parvoviruses a distinct safety advantage over other viral vector systems such as retroviruses and adenoviruses. Their potential utility in a clinical setting is considerably greater than that of other viral vectors because they package their genomes in such extremely rugged virions. Unlike retroviral vectors, for instance, parvoviral vectors would require little or no sophisticated equipment to maintain them as viable stocks. The half-life for MVMi infectivity is about nine months when stored in a simple diluent solution in an ordinary domestic refrigerator at about 8° C. In view of the foregoing, parvovirus is the preferred virus for use as viral vectors in therapy over other commonly used viral vectors.

Although there is little evidence for the rodent parvoviruses infecting humans by any natural route, direct parenteral inoculation of H-1 virus, a close relative of MVM, can result in transient viremia (Toolan et al., 1965, Proc. Soc. Exptl. Biol. Med., 119:711–715). When tested, the frequency of positive antibody titer to rodent parvoviruses in human populations was extremely low (Monif et al., 1965, J. Pediat., 67:253–256).

The chimeric viruses of the present invention also have utility in treating blood to be used for transfusion purposes. HIV, HTLV, and hepatitis are known to be transmitted by blood transfusion. Blood samples that were contaminated with HIV, HBV, HTLV and other viruses can be treated with the cytocidal, cytocidal-antagonist or non-cytocidal-antagonist vectors as described in Section 5.1. in order to effectively eliminate the infectious and/or pathogenic agents from the blood sample, prior to transfusion. Appropriate titers of the chimeric viruses would be used to treat blood samples prior to transfusion.

The chimeric viruses of the present invention are attractive for genetic therapy since they provide a stable delivery vector capable of being injected directly into the patient's bloodstream. This is a great advantage over current gene therapy approaches which require ex vivo culture and infection of either bone marrow derived or peripheral stem cells. The expense of treatment and limited availability of appropriate clinical centers, undoubtedly limits the benefits of such therapy to a tiny majority of the HIV infected population. The chimeric viruses of the present invention are not excluded from use in ex vivo cultures, however, their use in vivo has far greater advantages. Adenovirus, retrovirus, AAV and HSV have been previously used in genetic therapy approaches, and therefore comparable doses are applicable here, for use both in vivo and ex vivo. The dosage of parvovirus chimeric viruses can range from $10^9$ to $10^{12}$ infectious units for direct delivery. The dosage of parvovirus chimeric viruses can also be determined by the patient's lymphocyte count. Preferred dosage of parvovirus chimeric viruses range from 10 to 1000 virions per lymphocyte for direct delivery. The same dosages apply for use in ex vivo culture.

Chimeric viruses used for treating patients should preferably display a good "therapeutic index"; i.e., in the absence of the transactivation signal, activation of the chimeric virus may be leaky provided it does not result in significant cell killing.

6. EXAMPLE: CONSTRUCTION OF TAT-DEPENDENT, HUMAN LYMPHOTROPIC PARVOVIRUSES

Chimeric viruses were constructed in which specific elements present at the early promoter of a murine lymphotropic parvovirus MVMi, were replaced with TRE sequences derived from the HIV-1 genome. More specifically, the transactivation (TAR) region and upstream elements of the HIV-1 promoter were inserted into the MVMi regulatory region, using strategies based on the polymerase chain reaction (PCR). The resultant chimeric viruses replicated in infected human host cells in a tat-dependent manner, leading to cell lysis.

6.1. MATERIALS AND METHODS

6.1.1. CELL LINES AND PRIMARY CULTURES

Several human T cell lines were maintained in culture and they included Jurkat, Peer, H9, JMG2, HPB-ALL, and Molt-4 cells.

Several cell lines were engineered to express HIV-1 tat constitutively. The first series of tat-producer cell lines was derived from 324K cells, an SV40-transformed human fibroblast cell line capable of sustaining productive MVMP and MVMi growth (Tattersall et al., 1983, J. Virol., 46:944–55). The 324K cells were co-transformed with both a tat expression plasmid, either pSV2-tat or pCG-tat, in which tat was controlled by human cytomegalovirus immediate early promoter, and a dominant selectable marker, pSV2-neo. The resulting cell lines either did not express high enough levels of tat to support the replication of the MVM/HIV chimera, or they did not express such levels of tat in a genetically stable fashion.

Stable tat-producing cell lines were produced by inserting the dominant selectable marker gene, neo, in place of the E. coli β-galactosidase (β-gal) gene fragment, in the HIV-1 LTR-driven reporter vector pHIV-LacZ (Maio and Brown, 1988, J. Virol. 62:1398) to produce a construct referred to as pHIV-neo. This construct was used in subsequent co-transfection experiments with pSV2-tat or pCG-tat into 324K cells, followed by selection in medium containing different levels of G418. Cell lines resistant to G418 at levels up 500 μg/ml were selected.

6.1.2. CHIMERIC VIRAL CONSTRUCTS

MVMπ was derived from pMVMπ, a recombinant plasmid constructed to contain most of the capsid gene of the MVMi (lymphotropic strain) in the MVMp (prototype strain) background. The inclusion of this coat protein expanded the host range of the chimeric vector to human T lymphocytes.

MVMπ-Tar was derived from pMVMπ-Tar, a recombinant plasmid in which the Sp1 binding site, the TATAA box and much of 5' untranslated region of the MVM P4 transcripts are replaced by sequences from the upstream Sp1 through the entire stem structure of the transactivation region (TAR) of the HIV-1 promoter. This construct contains a unique Kpn1 restriction site at the downstream junction of the HIV and MVM sequences.

The PMVMπ-2 vector is a reconstruction of pMVMπ so that it contains the entire right hand end of pMVMi, thus removing an extra copy of a 65 base pair repeat of unknown function.

The pMVMπ-Tar-2 is the equivalent of pMVMπTar but its parent vector is pMVMπT2.

Viral genomes were manipulated as plasmids grown in E. coli. The left half of the MVM genome, containing both viral promoters and the non-structural genes, present in the infectious clone of the prototype strain, pMVMp-DB6, was recombined at the HindIII site (nt 2654) with the right half of pMVMπ, containing the capsid genes, to produce pMVMπ-2. This was done in order to provide a unique PmeI site (not present in the MVMi genome) at the downstream border of the essential left-end DNA replication origin (shown in FIG. 2), in combination with the capsid genes of MVMI, which would confer tropism for human T-lymphocytes on the resulting virus(es).

PCR was then performed to replace the sequences between this PmeI site and the common start codon of the MVM NS1 and NS2 genes with the analogous region from the HIV-1$_{LAI}$ 3' LTR, derived from pHIVlacZ (Maio & Brown, 1988, J. Virol. 62:1398). For MVMπ-Tar2, this exchange was designed to place the most upstream Sp1 binding site of the three present in the HIV LTR in register with the single Sp1 binding site present in the MVM P4 promoter, and to replace exactly a putative stem-loop structure in the MVM P4 transcript 5' untranslated region believed to be involved in attenuation of MVM P4 transcription (Ben-Asher and Aloni, 1984, J. Virol. 52:266), with the HIV TAR hairpin. Rightward priming of the PCR was performed with a 29mer primer [5'-CGC GTT TAA ACG GGA GCG TGG CCT GGG CG-3'] which incorporates the PmeI site and most of the two upstream Sp1 binding sites of HIV. Leftward priming was achieved using a 50mer primer [5'-CCA GCC ATG GTT AGT TGG gTA CcC TCT GGG TTC TCT AGT TAG CCA GAG AG-3'] which contains the NcoI site straddling the NS initiation codon, and makes two single base substitutions (lower case) between this site and the HIV TAR sequence which creates a KpnI site. The PCR product was cut with PmeI and NcoI, and engineered between these same sites in pMVMπ-2 by standard means.

6.1.3. SOUTHERN BLOT ANALYSIS

DNA purification and isolation. Total cell DNA was prepared from approximately $10^6$ infected or mock-infected cells washed in phosphate-buffered saline and resuspended in 20 mM Tris-150 mM NaCl-10 mM EDTA (pH 7.5). Proteinase K and sodium dodecyl sulfate (SDS) were added to final concentrations of 200 ug/ml and 1%, respectively, and samples were incubated at 60° C. for 4–5 hours. The DNA was extracted with phenol-chloroform and precipitated with ethanol. Following digestion with 100 ug of RNase A per ml, $5 \times 10^4$ cell equivalents of DNA were loaded per well, run on a 1.4% neutral agarose gel, and analyzed by Southern blotting.

Packaged viral DNA was assayed by freeze/thaw (3x) extraction of infected cells in 50 mM Tris, 0.5 mM EDTA, pH 8.7, followed by digestion with 50 ug/ml micrococcal nuclease at 37° C. for 30 min. The reaction was stopped by addition of EDTA to 20 mM and SDS to 0.5%, digested for 30 min at 37° C. with 80 ug/ml proteinase K, the samples denatured in 0.3M NaOH, run on a 1.4% alkaline agarose gel, and analyzed by Southern blotting.

Southern transfer (Southern, 1975, J. Mol. Biol. 98:503–17) was carried out with Hybond N (Amersham Corp., Arlington Heights, Ill.). The DNA was linked to the nylon by UV irradiation and prehybridized, and hybridization was performed with a random oligonucleotide labeled probe derived from the EcoRV (nt 383) to XbaI (nt 4345) of the MVMp genome, which detects both viral replicative duplexes and single-strand virion DNA.

6.1.4. WESTERN BLOT ANALYSIS

Detection of proteins. Cell extracts were fractionated by electrophoresis on 12% polyacrylamide SDS gels for detecting NS-1 and NS-2 or 10% polyacrylamide-SDS gels for detecting VP1 and VP2. Western immunoblots were performed as described by Cotmore & Tattersall (1990, Virology 177:477–87) with either a 1:1,000 dilution of a rabbit antibody specific for the common N terminus of NS-1 and NS-2 (Cotmore & Tattersall, 1986, J. Virol. 58:724–32) or a 1:600 dilution of a rabbit polyclonal antiserum raised against peptide epitopes present in MVMi and MVMp virions, which detects both VP1 and VP2. $^{125}$I-protein A was used to detect bound immunoglobulin.

6.1.5. CYTOTOXICITY ASSAY

Multiplicity-dependent killing by chimeric and wildtype MVM was assayed by analysis of surviving cells in a multiwell format. Briefly, cells were seeded in the wells of microtitre plates and varying quantities of virus added. At different times after infection, live and dead cells were quantitated by trypan blue staining. The results of these assays are used, in conjunction with the molecular analyses to evaluate the effects of changes within the chimeric promoter.

$$\text{viability index} = \frac{\text{total viable infected cells}}{\text{total viable control cells}} \times \text{culture dilution factor}$$

6.2. RESULTS

A recombinant chimeric parvovirus was constructed using two host range variants of the MVM. MVMp, the prototype strain, and MVMi, the lymphotropic strain, were reciprocally restricted for growth in each other's murine host cell type, which were fibroblasts and T-lymphocytes, respectively. This restriction occurs at an early step after viral entry into the host cell. The regions responsible for the ability of each strain to initiate infection in its appropriate host cell type, known as the allotropic determinants, had been mapped into a small region of the coat protein gene VP2 (Ball et al., 1992, J. Virol., 66:3415–23; Gardiner et al., 1988, J. Virol., 62:2605–13). This domain of the capsid is at or near the surface of the virion and appears to interact with developmentally-regulated host cell components in the establishment of productive infection.

The lymphotropic strain, MVMi, is able to bind to, enter and abundantly express its non-structural genes in several human T-cell lines, resulting in cell death. This effect is illustrated in FIG. 5 using H9 cells. Whereas even high multiplicities of MVMp, the prototype fibrotropic strain had little effect on H9 cell survival, multiplicities of infection (moi) as low as 1 pfu/cell of the lymphotropic strain, MVMi, resulted in extensive cell killing.

A recombinant MVMπ virus was then constructed to transfer most of the capsid gene of MVMi into the MVMp background (FIG. 6). This resultant virus was shown to kill H9 cells with efficiencies equivalent to MVMi (FIG. 5). Such recombinant virus was used as the basic tool in the development of tat-dependent T-cell tropic viral vectors, since its MVMp component contained a PmeI restriction cleavage site, missing in MVMi, which was essential for the HIV/MVM chimeric promoter strategy outlined below. Similar experiments have been repeated with several other human T-lymphocytic cell lines, namely Jurkat, Peer, JMG2, HFB-ALL and Molt-4, with essentially the same results.

Various parameters of MVM replication in H9 cells were examined. Infection with MVMπ at all multiplicities tested resulted in abundant expression of the major MVM non-structural protein NS1, as detected by the Western blot (upper panel of FIG. 7), using a specific anti-NS1 fusion antibody (Cotmore et al., 1986, J. Virol., 58:725–32). However, very little NS1 expression was detected in MVMp-infected H9 cells, even at 100 pfu/cell.

Viral DNA replication was analyzed by Southern blot (lower panel of FIG. 7), which produced a similar pattern. bundant amounts of the monomer duplex replicative form (RF) DNA were detected in MVMπ-infected cells, as well as significant accumulation of dimer RF DNA. Again, very little replicative DNA was detected in H9 cells infected with MVMp. H9 cells infected with both viruses contained single-stranded viral DNA, in approximate proportion to the input moi. This suggests both that the exclusion of the restricted virus in these cells occurs after binding to the cell surface receptor, as has been demonstrated in the mouse system (Spalholz et al., 1983, J. Virol., 46:937–943), and that there is relatively little progeny DNA synthesis even in H9 cells infected with MVMπ.

Infectivity measurements on single-step growth experiments supported the conclusion that MVMπ infection of these human T-cells was abortive, leading to high level production of viral gene products and RF DNA, but little progeny virus. These results indicate that encapsidation of MVM genome-based vectors in the MVMi coat would afford efficient delivery to, and expression in human T-lymphocytes.

6.2.1. CONSTRUCTION OF RECOMBINANT VECTORS COMPOSED OF PARVOVIRAL AND HIV REGULATORY REGIONS

Chimeric viruses were constructed using MVMπ as the basic tool, and the structure of the first chimera was referred to as MVMπ-Tar (FIGS. 2A–2D). The MVMπ-Tar construct was made by replacing certain MVM promoter elements with equivalent sequences of the HIV-1 transactivation region and the upstream elements of the HIV-1 promoter. This chimeric promoter was constructed back into the pMVMπ recombinant infectious clone, so as to allow production of lymphotropic progeny virus. The resulting plasmid, pMVMπTar, contained the region of HIV-1 extending from the upstream Sp1 binding site through the entire stem structure of the TAR element. As shown in FIGS.

2A–2BD, this insert replaced the Sp1 binding site present in the native MVM promoter (Pitluk et al., 1991, J. Virol., 65:6661–70), its TATAA box and much of the 51 untranslated region of the MVM P4 transcripts.

This strategy generated a recombinant viral genome which was replication competent, and which was dependent on the tat gene product if provided in trans. When co-transfected into monkey cos cells, which expressed SV40 T antigen, along with pSV2-tat, a plasmid which could replicate and express high levels of tat in these cells, both abundant NS1 expression and extensive MVM DNA replication were observed. Such expression and replication were not observed when the co-transfected plasmid was pSV2-neo. In addition, pRHEΔ, a derivative of the MVM infectious clone deleted for the essential palindrome at the viral right hand end did not replicate, and expressed NS1 poorly, when cotransfected with either "helper" plasmid. On the other hand, both expression and replication of the pMVMπ control infectious clone were detected at about equal levels with either co-transfected plasmid. Upon repetition of these experiments, the levels of pMVMπTar expression and replication in the presence of pSV2-tat generally paralleled those of pMVMπ in the presence of either SV40-based plasmid, and exceeded the levels of pMVMπTar expression and replication in the presence of pSV2-neo by about ten-fold. These results demonstrated a replication-competent MVM genome, chimeric for its promoter, which exhibited dependence on HIV-1 tat in trans for its expression.

6.2.2. CONSTRUCTION OF TAT PRODUCER CELL LINES

In order to produce the chimeric viral constructs, stable HIV-1-tat-expressing cell lines were developed by co-transfection of 324K cells with pHIV-neo and pSV2-tat or pCG-tat. The G418 resistant cell lines were evaluated by lipofectAMINE™-mediated transfection of pHIV-LacZ, followed by staining 60 hours later for β-gal activity. FIG. 8 shows the results of such an assay for one such cell line, 324K Tat-A3, compared with 324K B6-S13, a subclone of 324K, which did not express tat. The Tat-A3 cell line expressed a high level of active HIV tat from the transfected construct, as measured by the significant levels of β-gal staining in many of these cells, whereas pHIV-LacZ was expressed at low or undetectable levels in the control cells.

The Tat-A3 cell line was then evaluated for its ability to support the replication of the MVM/HIV promoter chimeric construct. The replication of transfected viral DNA was followed by Southern blot analysis. In the subclone which did not express tat, pMVMπ clearly replicated better than pMVMπTar. However, the chimeric viral genome replicated as efficiently as its parent in the cell line expressing tat. This confirmed the findings from cotransfection experiments that pMVMπTar was as replication competent as its MVMπ parent in the presence of tat.

6.2.3. EXPRESSION OF CHIMERIC VIRUSES IN PRODUCER CELL LINES

The observation that the Tar-containing construct did not produce high levels of progeny single-stranded DNA might be the result of a packaging defect. Thus, both pMVMπ and pMVMπTar plasmids were reconstructed so that they contained the entire right hand end of pMVMi. This process removed the extra copy of the 65 base repeat of unknown function to produce pMVMπTar-2 and pMVMi2. These plasmids were then analyzed by transfection into Tat-A3 and control cells, followed by analysis for packaged genomes. In order to examine the amount of packaged virus produced by transfection, transfected cells were concentrated and extracted under conditions which released virus into the supernatant, and an alkaline gel of the extracts was subjected to Southern blot analysis. When the viral nucleic acid species released into the supernatant of such extracts were digested with micrococcal nuclease prior to alkaline disruption of virions, the signal from packaged genomes could clearly be seen.

The result of such an experiment is shown in FIG. 9. Whereas nuclease-resistant 5 kb genomes were abundant in extracts of both 324K derivative cell lines transfected with pMVMπ-2, packaged pMVMπTar-2 genomes were found only in the lysate of the tat-expressing cell line Tat-A3. These results support the following conclusions: (1) MVM/HIV chimeric promoter plasmids could indeed be recovered as infectious virus; (2) the resulting chimeric virus was dependent upon HIV-1 tat provided in trans for efficient growth; and (3) the Tat-A3 cell line was useful as a host cell for propagating such viruses. Although MVMπTar-2 virus stocks were expanded in the Tat-A3 cell line, and the cells developed cytopathic effect (CPE) upon continued passage in the presence of the virus, no plaque formation was observed on monolayers of these cells.

The dependence of MVMπTar-2 virus upon HIV tat for gene expression and DNA replication was further confirmed by the experiment shown in FIG. 10. Western blots of total non-structural proteins did not detect any MVMπTar-2 gene expression in the $tat^-$ cell line, whereas NS1 synthesis was readily detected in Tat-A3 cells infected with this chimeric virus. Similarly, viral RF DNA was readily detectable in Tat-A3 cells infected with either virus, but it accumulated only in non-tat-expressing cells infected with MVMπ-2, but not with MVMπTar-2. Interestingly, although the Southern blots confirmed that the input genome number was well matched, these analyses showed that gene expression and DNA replication were somewhat lower for MVMπTar-2, compared to MVMπ-2, in Tat-A3 cells, as measured by NS gene expression in FIG. 10.

6.2.4. REPLICATION AND CYTOTOXIC EFFECTS OF CHIMERIC VIRUSES IN HUMAN LYMPHOCYTES

In order to ascertain the tat-regulated gene delivery by chimeric viruses in human lymphocytes, H9 cells were infected by various viral constructs. Firstly, it was confirmed that the reconstruction of MVMπ to MVMπ-2 had not affected its ability to express its non-structural genes and replicate its DNA in H9 cells (FIG. 11). While MVMπ-2 abundantly expressed its non-structural proteins in H9, as did its "parent" MVMπ (compare FIG. 5), the expression of NS1 in H9 cells infected with MVMπTar-2 was barely detectable. Southern blotting of the samples taken at 4 hours following infection, but before viral DNA replication had begun, demonstrated approximately equal numbers of input genomes of each virus. However, there was no detectable amplification of the MVMπTar-2 genomes, as compared to those of MVMπ-2, even 26 hours post infection. These results indicate that MVMπTar-2 failed to initiate sufficient NS1 gene expression to support viral DNA replication in the absence of tat in H9 cells.

The results of cytotoxicity assays also indicated that the weak NS1 expression in MVMπTar-2 infected H9 cells was too low to affect the host cells' viability. A small decrease in the viability index could be seen upon infection with MVMπTar-2, but it was very low when compared to the >90% killing seen with the same multiplicity of MVMπ-2 over the same time period. In addition, this decrease in total viable cells in the MVMπTar-2 infected culture, compared to the uninfected control, appeared to be due more to a transient decrease in the proliferation rate of the infected cells, than to an increase in trypan blue-staining cells. Thus, the tat-dependent chimeric virus would not induce significant lysis in non-tat expressing cells.

In order to further confirm the tat-dependence of MVMπTar-2 in human cells, two additional cell lines were tested: the Jurkat cell line and its derivative, Jurkat-tat, which constitutively expressed the HIV-1 transactivator protein. The parental Jurkat cell line was extremely sensitive to killing by MVMπ-2, whereas it was much more resistant to MVMπTar-2 (FIG. 12). Nonetheless, its growth rate was marginally slowed by infection with the chimeric virus and it was clearly less resistant to MVMπTar-2 than was H9. Significantly, the Jurkat-tat cell line was killed almost equally as well by either virus, but, in turn, was not nearly as sensitive as its Jurkat parent. While this could be interpreted as an intrinsically negative effect of tat on MVM growth, the absence of such an effect in the 324K cell system suggested that this difference was more likely due to variability among subclones of the same continuous transformed cell line.

Examination of viral gene expression in these two cell lines revealed another difference from the H9 results. The results in FIG. 12 demonstrated an appreciable expression of MVMπTar-2 NS1 in Jurkat cells in the absence of tat. These experiments were repeated with Jurkat cells from two different sources, with the same result. Therefore, there was either some cell-specific leakiness in the transcriptional attenuation due to the HIV-1 TAR sequence, or that Jurkat cells expressed a factor(s) which interacted with the chimeric promoter to increase its basal level of transcription.

One possible result would be that a few cells sustained high level NS1 expression and subsequently died, and that in the majority of cells, expression off the chimeric promoter was as completely shut down as it was in H9 cells. Alternatively, there might be a gradation of NS1 synthesis across the cell population, and a threshold level existed below which cells might stop growing but did not die, and eventually started to grow again. Such a scenario would fit with the report of Caillet-Fauquet et al., (1990, EMBO J., 9:2989–95) who observed low levels of NS1 expression, compatible with colony formation in the absence of dexamethasone, for human cells transformed with an MVM non-structural gene cassette under the control of the murine mammary tumor virus (MMTV) LTR. Some of these cells exhibited high enough basal expression of NS1 to transactivate a P38-driven reporter gene transfected into them. In general, they found that the higher the basal level of NS1 expression shown by a cell line, the more sensitive it was to dexamethasone inhibition in a colony forming assay (Caillet-Fauquet et al., 1990, EMBO J., 9:2989–95; Rommelaere, J., personal communication), suggesting that these cells were expressing NS1 at below a threshold of toleration, but that induction of the MMTV promoter increased this expression to a level incompatible with further growth.

7. EXAMPLE: ISOLATION OF TARGET CELLS FROM WHOLE BLOOD AND INFECTION WITH CHIMERIC VIRUS

The experiments described in this section demonstrate that freshly isolated human peripheral blood mononuclear cells were susceptible to infection by the murine lymphotropic MVMi and its derivatives.

7.1. MATERIALS AND METHODS

Target cells were prepared from heparinized whole blood obtained from two healthy donors, by fractionation on Ficoll-Lyte followed by culture for 72 hours in RPMI 1640, supplemented with 15% fetal bovine serum and 5 ug/ml PHA-P. After 48 hours of growth in the presence of interleukin-2 (IL2), these proliferating mononuclear cells were all $IL2R^+$, and approximately 55% $CD4^+$, 45% $CD8^-$, with almost no NK or B lymphocytes, by flow cytometric analysis. At this point the cells were infected at 10 pfu/cell with MVMp, MVMi, MVMπ-2 or MVMπTar-2, as described for H9 cells in FIG. 10. At 4 hours 20 and 24 hours after infection, cells were taken for DNA analysis by Southern blot. At 24 hours, cells were also prepared for Western blot analysis and for immunofluorescence.

In Southern blot analysis of DNA replication, the signal from single stranded band at 4 hours indicated that the cells in each of the cultures bound approximately the same amount of input virus. In cells infected with MVMi and MVMπ-2, there was clear evidence of monomer RF formation, indicative of viral DNA replication. Interestingly, there was also measurable viral DNA replication in the MVMπTar-2 infected cells, whereas there was no signal detectable in the MVMp-infected cells. Cells from each culture were stained with an anti-NS1/2 common region antibody, and probed in Western blots with the same antibody. Either technique revealed relatively little expression of NS1/2 in the cells infected with MVMp or MVMπTar-2, whereas infection was demonstrated in the MVM1 and MVMπ-2 cultures. Therefore, there was a considerable fraction of the proliferating cells, predominantly small T-lymphocytes, which was capable of sustaining infection by MVM when delivered in the lymphotropic virus coat. In contrast, the virus containing the chimeric HIV/MVM promoter did not express high levels of NS1/2, but showed a low level expression in most of the cells in the population. Occasional brightly fluorescing cells were seen in cultures infected with MVMP, which paralleled the restrictive infection of murine T-cell lines with this fibrotropic virus (Tattersall and Bratton, 1983, J. Virol., 46:944–55).

The growth rates and viability of these cultures paralleled the NS1/2 expression and DNA replication results. By six days after infection, only 10% of the MVMi-infected, and 22% of the MVMπ-2 infected cultures were still viable, and the cell numbers had not increased since the 24 hour time point. However, essentially all of the MVMp-infected and the majority of MVMπTar-2 infected cells continued to proliferate in parallel with the uninfected control culture, and maintained viabilities of 95% and 85%, respectively, by day six.

These results demonstrate the ability of a murine lymphotropic parvovirus to infect primary human T cells. Additionally, the low level of expression and lack of cell killing exhibited by MVMπTar-2, as compared to MVMi and MVMπ-2, indicate that such a chimeric promoter-containing virus is restricted for expression of its non-structural genes in the absence of tat in such primary T cells. Thus, such a virus is capable of infecting human lymphocytes, but remains non-replicative and non-cytolytic in normal cells.

The present invention is not to be limited in scope by the exemplified embodiments which are intended as illustrations of single aspects of the invention, and any clones, DNA or amino acid sequences which are functionally equivalent are within the scope of the invention. Indeed various modifications of the invention in addition to those described herein will become apparent to those skilled in the art from the foregoing description and accompanying drawings. Such modifications are intended to fall within the scope of the appended claims.

It is also understood that all base pair sizes given for nucleotides are approximate and are used for purposes of description. Each publication cited herein is incorporated by reference in its entirety.

8. DEPOSIT OF MICROORGANISMS

The following microorganisms were deposited with the American Type Culture Collection (ATCC), Rockville, Md., on Jul. 21, 1995 and were assigned the indicated accession numbers:

| Microorganism | Clone | ATCC Accession No. |
|---|---|---|
| NB324K-tat-A3.2 | | CRL 11961 |
| pMVMπTar-2 | | ATCC 97227 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A replication competent chimeric cytocidal parvovirus that infects human host cells, comprising a chimeric regulatory region that initiates and completes the replicative process without the addition of parvoviral genes in trans, of the chimeric cytocidal parvovirus in response to a regulatory factor produced by virus infected human host cells.

2. The chimeric cytocidal virus of claim 1 in which a region of the chimeric viral genome that is not encoding a viral protein required for viral replication contains a nucleotide sequence that encodes a product that inhibits the expression or activity of a gene product involved in the virus infected host cell disease pathway.

3. The chimeric virus of claims 1 or 2 which is a pMVMπ parvovirus.

4. The chimeric virus of claim 3 in which the pathogen is HIV, HBV, or HTLV.

5. The chimeric virus of claims 1 or 2 which is a pMVMπ-Tar parvovirus.

6. The chimeric virus of claim 1 or 2 in which the chimeric virus replicates in response to a virus encoded transactivator expressed by a virus infected host cell.

7. A replication competent chimeric cytocidal parvovirus that infects HIV infected human host cells comprising a chimeric regulatory region that initiates and completes replication of the chimeric cytocidal parvovirus without the provision of additional parvovival genes in trans, in response to a HIV-tat produced by HIV-infected host cells.

8. The chimeric cytocidal virus of claim 1, in which a region of the chimeric viral genome that is not encoding viral protein required for viral replication contains a nucleotide sequence that encodes a product that inhibits HIV replication.

9. The chimeric cytocidal-antagonist virus of claim 8 in which the product that inhibits HIV replication is a mutant form of HIV envelope or Rev that inhibits HIV replication via a dominant-negative effect.

10. The chimeric cytocidal-antagonist virus- of claim 8 in which the product that inhibits HIV replication is an antisense, ribozyme or triple helix that inhibits expression of an HIV gene product required for HIV replication.

11. The chimeric virus of claim 7 or 8 which is a pMVMπ parvovirus.

12. The chimeric virus of claim 7 or 8 which is a pMVMπ-Tar parvovirus.

* * * * *